United States Patent
Faulks et al.

[19]

[11] Patent Number: 5,853,402
[45] Date of Patent: Dec. 29, 1998

[54] ABSORBENT ARTICLE HAVING A COMPOSITE ABSORBENT CORE

[75] Inventors: Michael John Faulks, Neenah; Thomas Walter Odorzynski, Green Bay, both of Wis.

[73] Assignee: Kimberly-Clark Worldwide, Inc., Neenah, Wis.

[21] Appl. No.: 807,848

[22] Filed: Feb. 26, 1997

Related U.S. Application Data

[63] Continuation of Ser. No. 344,777, Nov. 23, 1994, abandoned.

[51] Int. Cl.[6] .................................................. A61F 13/15
[52] U.S. Cl. .................... 604/378; 604/385.1; 604/369
[58] Field of Search ................................. 604/358, 378, 604/385.1, 367–369

[56] References Cited

U.S. PATENT DOCUMENTS

| | | |
|---|---|---|
| 3,371,667 | 3/1968 | Morse . |
| 3,431,911 | 3/1969 | Meisel, Jr. . |
| 3,461,872 | 8/1969 | McConnell et al. . |
| 3,563,243 | 2/1971 | Lindquist . |
| 3,887,408 | 6/1975 | Hoey . |
| 3,901,240 | 8/1975 | Hoey . |
| 3,916,900 | 11/1975 | Breyer et al. . |
| 3,993,074 | 11/1976 | Murray et al. . |
| 4,000,028 | 12/1976 | Hoey . |
| 4,055,184 | 10/1977 | Karami . |
| 4,068,666 | 1/1978 | Shiff . |
| 4,069,366 | 1/1978 | Hoey . |
| 4,098,728 | 7/1978 | Rosenblatt . |
| 4,132,839 | 1/1979 | Marans et al. . |
| 4,191,815 | 3/1980 | Jourquin et al. . |
| 4,287,251 | 9/1981 | King et al. . |
| 4,306,559 | 12/1981 | Nishizawa et al. . |
| 4,338,371 | 7/1982 | Dawn et al. ....................... 604/378 |
| 4,364,992 | 12/1982 | Ito et al. . |

(List continued on next page.)

FOREIGN PATENT DOCUMENTS

| | | |
|---|---|---|
| 0 122 803 | 10/1984 | European Pat. Off. . |
| 0 165 807 | 12/1985 | European Pat. Off. . |
| 0 312 118 | 4/1989 | European Pat. Off. . |
| 0 343 941 | 11/1989 | European Pat. Off. . |
| 0 397 110 | 11/1990 | European Pat. Off. . |
| 0425270 A2 | 5/1991 | European Pat. Off. . |
| 0427219 A2 | 5/1991 | European Pat. Off. . |
| 0 572 033 | 12/1993 | European Pat. Off. . |
| 1 527 300 | 10/1978 | United Kingdom . |
| 2 168 612 | 6/1986 | United Kingdom . |
| 2233235 | 1/1991 | United Kingdom . |
| 2243327 | 10/1991 | United Kingdom . |
| 2 279 013 | 12/1994 | United Kingdom . |
| WO 90/01311 | 2/1990 | WIPO . |
| 90 14061 | 11/1990 | WIPO . |
| WO 91/00719 | 1/1991 | WIPO . |
| 91 11161 | 8/1991 | WIPO . |
| WO 92/11830 | 7/1992 | WIPO . |
| WO 92/11831 | 7/1992 | WIPO . |
| 94 28839 | 12/1994 | WIPO . |

Primary Examiner—John G. Weiss
Assistant Examiner—Dennis Ruhl
Attorney, Agent, or Firm—Jeffrey B. Curtin

[57] ABSTRACT

Disclosed is a distinctive composite absorbent core and an absorbent article incorporating the same. The absorbent core comprises at least one absorbent portion and at least one porous resilient portion. The porous resilient portion is located adjacent the absorbent portion and has a wet compression recovery of at least about 85 percent. The porous resilient portion may have a basis weight of from about 50 to about 250 grams per square meter and a density of not more than about 0.050 grams per cubic centimeter. In a particular aspect, the porous resilient portion has a mean pore size of at least about 1.50 millimeters. In a particular aspect, the absorbent article incorporates the absorbent core and has an absorbent core crotch width dimension which may be no more than about 6.35 centimeters. In another particular aspect, the absorbent article also has a fluid intake rate of at least about 10 milliliters per second.

51 Claims, 8 Drawing Sheets

U.S. PATENT DOCUMENTS

| | | |
|---|---|---|
| 4,394,930 | 7/1983 | Korpman . |
| 4,410,324 | 10/1983 | Sabee . |
| 4,410,571 | 10/1983 | Korpman . |
| 4,415,388 | 11/1983 | Korpman . |
| 4,425,130 | 1/1984 | DesMarais . |
| 4,433,972 | 2/1984 | Malfitano . |
| 4,534,769 | 8/1985 | De Jonckheere et al. . |
| 4,592,751 | 6/1986 | Gegelys . |
| 4,610,678 | 9/1986 | Weisman et al. . |
| 4,613,543 | 9/1986 | Dabi . |
| 4,643,726 | 2/1987 | Gegelys . |
| 4,676,785 | 6/1987 | Battista . |
| 4,681,577 | 7/1987 | Stern et al. . |
| 4,685,914 | 8/1987 | Holtman . |
| 4,731,391 | 3/1988 | Garvey . |
| 4,740,528 | 4/1988 | Garvey et al. . |
| 4,798,603 | 1/1989 | Meyer et al. ............ 604/378 |
| 4,834,735 | 5/1989 | Alemany et al. . |
| 4,847,134 | 7/1989 | Fahrenkrug et al. . |
| 4,880,419 | 11/1989 | Ness . |
| 4,891,258 | 1/1990 | Fahrenkrug . |
| 4,902,565 | 2/1990 | Brook . |
| 4,950,262 | 8/1990 | Takagi . |
| 4,988,344 | 1/1991 | Reising et al. . |
| 5,147,345 | 9/1992 | Young et al. . |
| 5,192,606 | 3/1993 | Proxmire et al. . |
| 5,294,478 | 3/1994 | Wanek et al. ............ 604/378 |

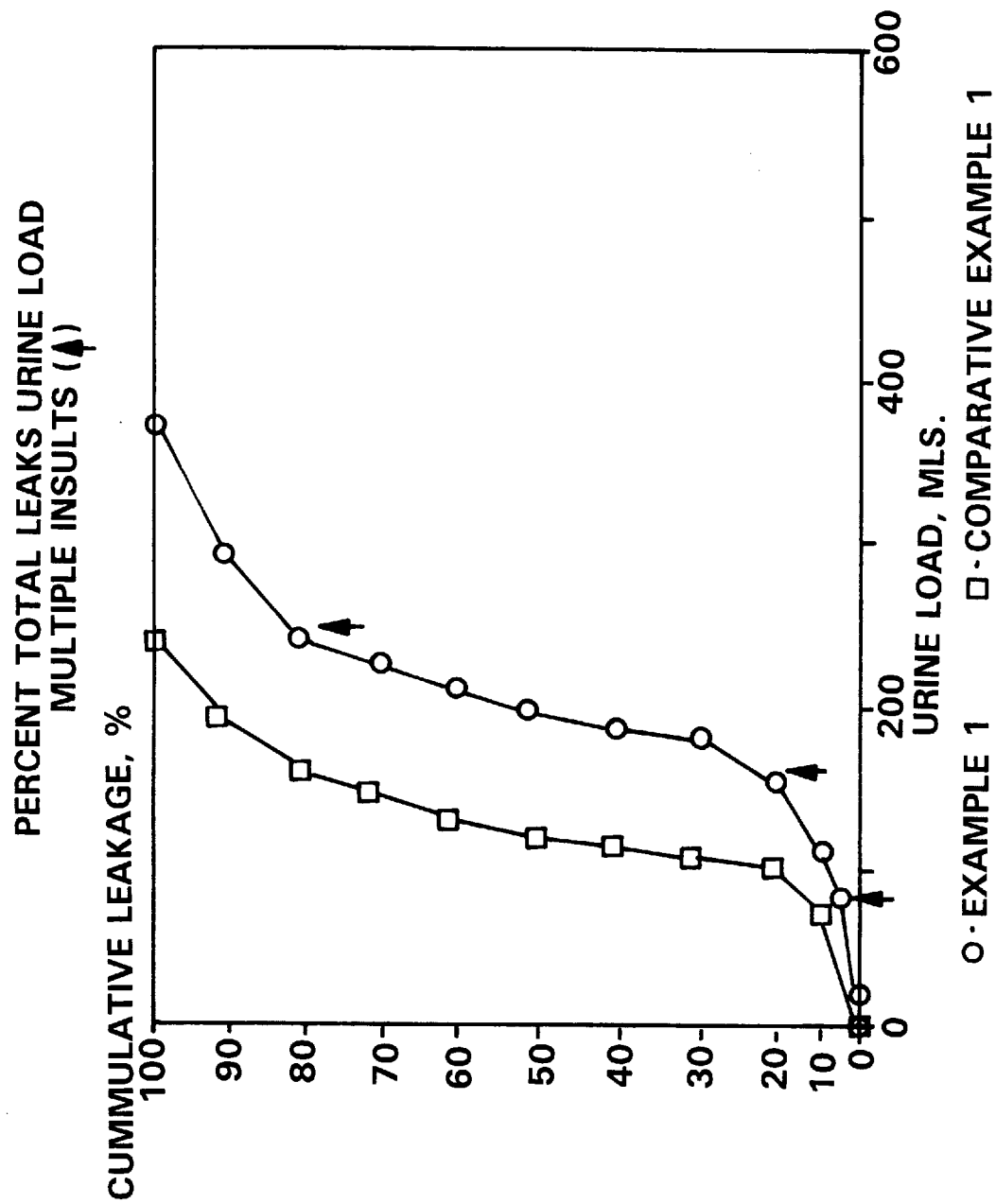

ABSORBENT ARTICLE HAVING A COMPOSITE ABSORBENT CORE

This application is a continuation of application Ser. No. 08/344,777 entitled "ABSORBENT ARTICLE HAVING A COMPOSITE ABSORBENT CORE" and filed in the U.S. Patent and Trademark Office on Nov. 23, 1994 now abandoned. The entirety of this application is hereby incorporated by reference.

BACKGROUND OF THE INVENTION

1. Field of the Invention

The present invention relates to an absorbent article having a composite absorbent core. The invention more particularly relates to composite absorbent cores which have a relatively narrow crotch width for improved fit and performance.

2. Description of the Related Art

It is desired that absorbent articles such as diapers, training pants or incontinence garments both provide a close, comfortable fit about the wearer and contain body exudates. Absorbent articles having a relatively narrow crotch width have been found to provide an improved fit about the wearer which improves the aesthetics of the article and increases the wearer's mobility. However, absorbent articles having a narrow crotch width commonly fail or leak at the legs before the total absorbent capacity of the absorbent article is utilized. Typically, the premature leakage at the legs is due to a variety of reasons. For example, insufficient distribution of fluid may occur in absorbent articles having a narrow crotch width. As such, the relatively small absorbent capacity in the crotch portion of such absorbent articles has become saturated with fluid and resulted in excessive pooling of the fluid on the bodyfacing surface of the absorbent article. The pooled fluid can then leak from the leg opening of the absorbent article and soil the outer clothing or bedding of the wearer.

Moreover, insufficient resiliency of the absorbent structure in the narrow crotch absorbent articles has resulted in premature leakage around the leg openings of the absorbent article when the wearer has exerted compressive forces on the absorbent article. For example, conventional absorbent structures which generally contain cellulosic fibers and high absorbency particles have lost their resiliency and tend to collapse when wetted. The collapsed absorbent structure has resulted in a loss in absorbent capacity of the absorbent structure due to the loss in void volume. In addition, the collapsed absorbent structure has not been able to distribute any excess or successive amounts of fluid.

Attempts to alleviate the leakage of fluid have included providing physical barriers such as containment flaps in combination with elastic leg gathers. High-absorbency particles have also been included in the absorbent structure to increase the fluid holding capacity in various regions of the absorbent article.

However, such attempts have not sufficiently reduced the amount of leakage in absorbent articles and, in particular, absorbent articles having a narrow crotch width. The addition of containment flaps and elastic leg gathers has helped reduce leakage but may result in absorbent articles having an increased crotch width that may not provide the proper fit about the wearer. Moreover, the use of high-absorbency particles may limit the ability of the saturated area of the absorbent structure to distribute any excess fluid to the remaining unsaturated areas of the absorbent structure. For example, the high-absorbency particles swell as fluid is absorbed which may tend to block distribution channels or paths for the excess fluid to reach other portions of the absorbent structure. This phenomenon is commonly referred to as "gel blocking." The swelling of the high-absorbency particles also reduces the void volume of the absorbent structure. Further, the high-absorbency particles have typically been unable to absorb the fluid exudates at the rate they are excreted from the wearer which also has resulted in excessive pooling and leakage.

Despite the attempts to develop improved absorbent structures, there remains a need for absorbent structures which can function in absorbent articles having a very narrow crotch width. There is a need for an absorbent structure having a very narrow crotch width that can effectively distribute fluids such that an increased amount of the absorbent capacity of the absorbent structure is utilized. Moreover, there is a need for an absorbent structure which has sufficient resiliency, both wet and dry, such that it is capable of maintaining sufficient void volume under typical loading conditions.

SUMMARY OF THE INVENTION

In response to the difficulties and problems discussed above, a new absorbent article having a composite absorbent core has been discovered.

Generally stated, the present invention can provide a distinctive composite absorbent core which is suitable for use in an absorbent article. The absorbent core comprises at least one absorbent portion and at least one porous resilient portion. The porous resilient portion has a void volume and is located adjacent the absorbent portion. The porous resilient portion also has a wet compression recovery of at least about 85 percent. The porous resilient portion may have a basis weight of from about 50 to about 250 grams per square meter and a density of not more than about 0.050 grams per cubic centimeter. In a particular aspect, the porous resilient portion has a mean pore size of at least about 1.5 millimeters. The composite absorbent core may also include a surge portion. In a particular aspect, the composite absorbent core may also have a crotch width dimension which is no more than 6.35 centimeters (2.5 inches).

In another aspect, the present invention can provide a composite absorbent core which is suitable for use in an absorbent article. The absorbent core has a front section, a back section and a crotch section which extends between and connects the front section to the back section. The absorbent core comprises a first absorbent portion which is located in the back section of the absorbent core and a second absorbent portion which is located in the front section and the crotch section of the absorbent core. The absorbent core further comprises a first porous resilient portion which has a void volume and is located between the first and the second absorbent portions. In a particular aspect, the first porous resilient portion has a wet compression recovery of at least about 85 percent.

In another aspect, the present invention can provide an absorbent article having a front portion, a rear portion and a crotch portion which extends between and connects the front portion to the rear portion. The absorbent article comprises an outer cover, a bodyside liner which is superposed on the outer cover, and a composite absorbent core which is located between the outer cover and the bodyside liner. The absorbent core comprises at least one absorbent portion and at least one porous resilient portion which has a void volume and is located adjacent the absorbent portion. The porous resilient portion has a wet compression recovery of at least about 85 percent. The absorbent article may have an article crotch width dimension which is no more than about 12.7 centimeters (5.0 inches). The absorbent article may also include at least one surge portion which may be located adjacent the porous resilient portion. In a particular aspect, the absorbent article also has a fluid intake rate of at least about 10 milliliters per second.

The present invention can advantageously provide an absorbent article having an absorbent structure which has a relatively narrow crotch width and is capable of efficiently distributing fluids to more effectively utilize the absorbent capacity of the absorbent article. The absorbent article can provide a conforming, comfortable fit about the wearer while sufficiently containing body exudates. A resilient porous component of the invention can provide sufficient void volume in the absorbent article and more efficiently distribute the fluid to unsaturated areas of the absorbent structure of the absorbent article. As a result, the absorbent article of the present invention can reduce the amount of leakage around the leg openings of the absorbent article even when the width of the crotch section of the absorbent article is very narrow.

BRIEF DESCRIPTION OF THE DRAWINGS

The present invention will be more fully understood and further advantages will become apparent when reference is made to the following detailed description of the invention and the accompanying drawings. The drawings are merely representative and are not intended to limit the scope of the appended claims.

FIG. 11 representatively shows a graph of the data obtained in the Examples demonstrating the load retained at leak.

DETAILED DESCRIPTION OF THE INVENTION

The present invention provides an absorbent article having a composite absorbent core. The composite absorbent core includes at least one absorbent portion and at least one porous resilient portion. The absorbent article and composite absorbent core may be configured to have a narrow crotch width dimension to provide an improved fit about the wearer.

The absorbent article of the present invention will be described in terms of a diaper article adapted to be worn by infants about the lower torso. It is understood that the absorbent article of the present invention is equally applicable to other articles such as adult incontinent products, training pants, feminine care products and the like. Moreover, it should be understood that the potential uses of the composite absorbent core of the present invention need not be limited to use in absorbent articles. For example, the composite absorbent core of the present invention may also be used in surgical bandages, sponges and the like.

Figure 1A:
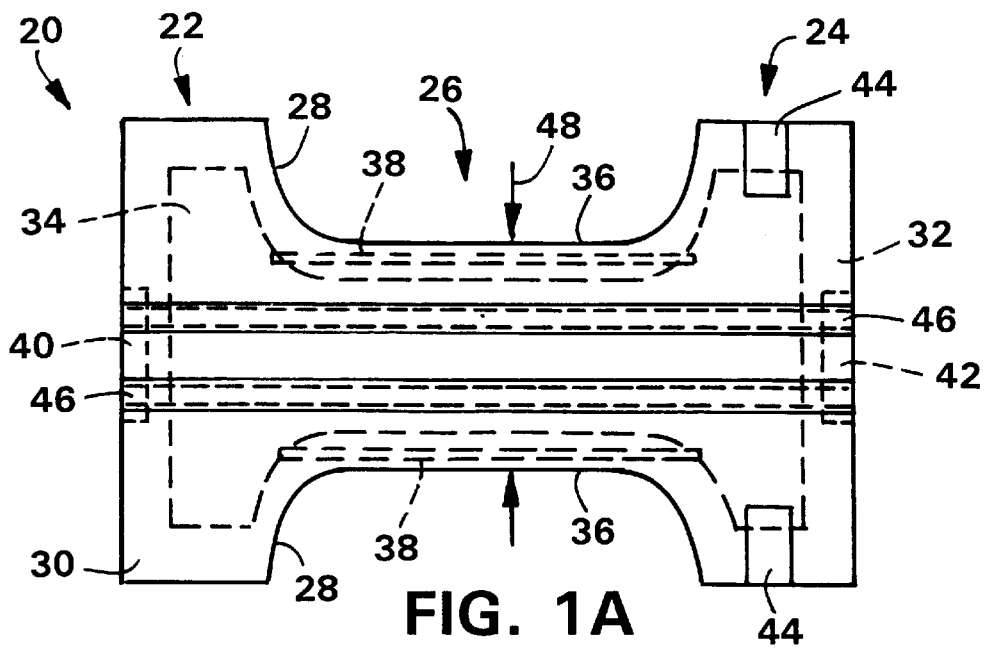
FIG. 1A representatively shows a top plan view of an absorbent article of the present invention.
Figure 1B:
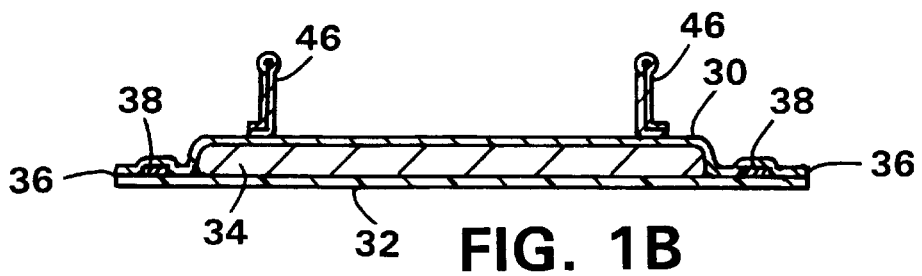
FIG. 1B representatively shows a lateral cross-sectional view of the absorbent article of FIG. 1A wherein the containment flaps have been urged into a generally upright configuration.
Figure 1C:
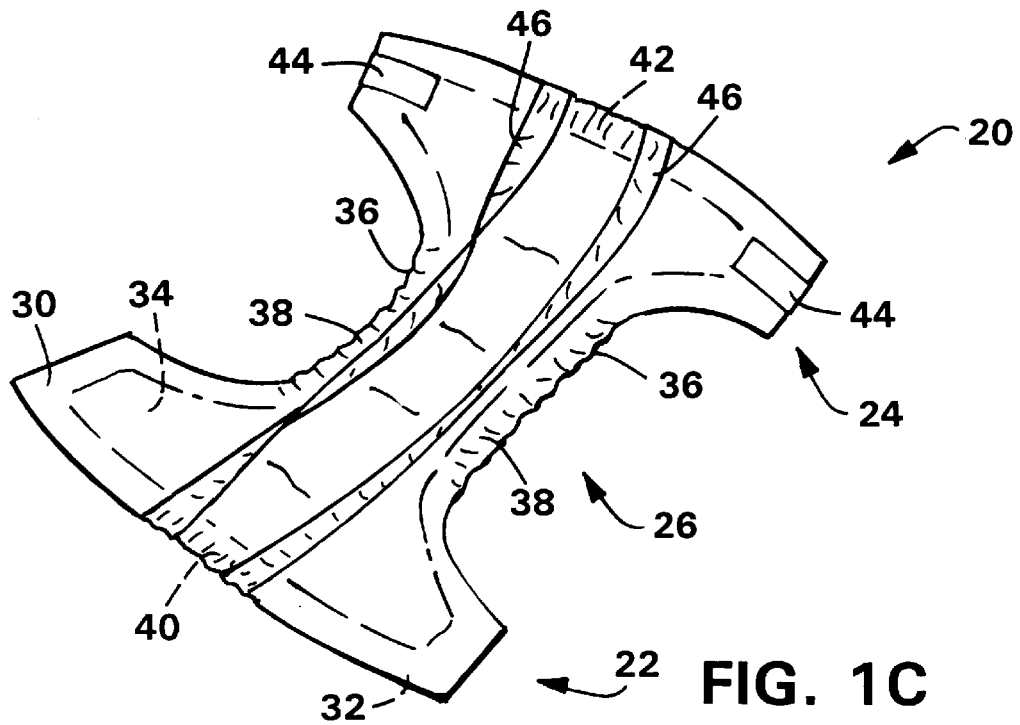
FIG. 1C representatively shows a perspective view of the absorbent article of FIG. 1A wherein the leg elastics have contracted and gathered the side edges of the absorbent article.

FIGS. 1A–1C representatively illustrate an absorbent article 20 of the present invention. The surface of the article which contacts the wearer is facing the viewer. As representatively illustrated in FIGS. 1A–1C, the absorbent article 20 defines a front portion 22, a rear portion 24, and a crotch portion 26 connecting the front portion 22 and the rear portion 24. The absorbent article 20 includes a bodyside liner 30, an outer cover 32 and a composite absorbent core 34 located between the bodyside liner 30 and the outer cover 32. As used herein, reference to a front portion refers to that part of the absorbent article which is generally located on the front of a wearer when in use. Reference to the rear portion refers to the portion of the article generally located at the rear of the wearer when in use, and reference to the crotch portion refers to that portion which is generally located between the legs of the wearer when in use.

The crotch portion 26 has opposite longitudinal side portions 28 which include a pair of elasticized, longitudinally-extending leg cuffs 36. The leg cuffs 36 are generally adapted to fit about the legs of a wearer in use and serve as a mechanical barrier to the lateral flow of body exudates. The leg cuffs 36 are elasticized by a pair of leg elastics 38. The absorbent article 20 further includes a front waist elastic 40 and a rear waist elastic 42. The rear portion 24 of the absorbent article 20 further includes a fastening means 44 which is intended to hold the absorbent article 20 about the waist of the wearer when in use. The absorbent article 20 may also include a pair of containment flaps 46 which extend longitudinally along the absorbent article 20 and are also adapted to provide a barrier to the flow of body exudates. It should be recognized that individual components of the absorbent article 20, such as the elastic members, may be optional depending upon the intended use of the absorbent article 20.

The bodyside liner 30 of the absorbent article 20, as representatively illustrated in FIGS. 1A–1C, suitably presents a bodyfacing surface which is intended to be worn adjacent the body of the wearer and is compliant, soft feeling and nonirritating to the wearer's skin. Further, the bodyside liner 30 may be less hydrophilic than the composite absorbent core 34, to present a relatively dry surface to the wearer, and may be sufficiently porous to be liquid permeable, permitting liquid to readily penetrate through its thickness. A suitable bodyside liner 30 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 30 is suitably employed to help isolate the wearer's skin from fluids held in the composite absorbent core 34.

Various woven and nonwoven fabrics can be used for the bodyside liner 30. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In particular embodiment of the present invention, the bodyside liner 30 comprises a nonwoven, spunbond, polypropylene fabric composed of about 2.8–3.2 denier fibers formed into a web having a basis weight of about 22 grams per square meter and a density of about 0.06 grams per cubic centimeter. The fabric is surface treated with about 0.28 weight percent of a surfactant commercially available from Rohm and Haas Co. under the trade designation Triton X-102.

The outer cover 32 of the absorbent article 20, as representatively illustrated in FIGS. 1A–1C, may suitably be composed of a material which is either liquid permeable or liquid impermeable. It is generally preferred that the outer cover 32 be formed from a material which is substantially impermeable to fluids. For example, a typical outer cover can be manufactured from a thin plastic film or other flexible liquid-impermeable material. For example, the outer cover 32 may be formed from a polyethylene film having a thickness of from about 0.012 millimeters (0.5 mil) to about 0.051 millimeters (2.0 mils). If it is desired to present the outer cover 32 with a more clothlike feeling, the outer cover 32 may comprise a polyethylene film having a nonwoven web laminated to the outer surface thereof, such as a spunbond web of polyolefin fibers. For example, a polyethylene film having a thickness of about 0.015 millimeters (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounces per square yard). Methods of forming such clothlike outer covers are known to those skilled in the art.

Further, the outer cover 32 may be formed of a woven or nonwoven fibrous web layer which has been totally or partially constructed or treated to impart a desired level of liquid impermeability to selected regions that are adjacent or proximate the composite absorbent core 34. Still further, the outer cover 32 may optionally be composed of a microporous "breathable" material which permits vapors to escape from the composite absorbent core 34 while still preventing liquid exudates from passing through the outer cover 32.

The bodyside liner 30 and outer cover 32 are generally adhered to one another so as to form a pocket in which the composite absorbent core 34 is located. The bodyside liner 30 and outer cover 32 may be adhered directly to each other around the outer periphery of the absorbent article 20 by any means known to those skilled in the art such as adhesive bonds, sonic bonds or thermal bonds. For example, a uniform continuous layer of adhesive, a patterned layer of adhesive, a sprayed or meltblown pattern of adhesive or an array of lines, swirls or spots of adhesive may be used to affix the bodyside liner 30 to the outer cover 32. Such bonding means may also be suitable for attaching other components of the composite absorbent core and absorbent article of the present invention together. The leg cuffs 36 are suitably formed by portions of the outer cover 32, and/or bodyside liner 30, which extend beyond the longitudinal sides of the composite absorbent core 34. Naturally, the leg cuffs 36 can also be formed from separate materials which are attached to the outer cover 32 and/or bodyside liner 30.

The leg cuffs 36, as representatively illustrated in FIGS. 1A–1C, may include leg elastics 38. Waist elastics 40 and 42 may also be provided. The leg elastics 38 are arranged to draw and hold the absorbent article 20 against the legs of the wearer. The waist elastics 40 and 42 are also arranged to draw and hold the absorbent article 20 against the wearer. Materials suitable for use in forming leg elastics 38 and waist elastics 40 and 42 are known to those skilled in the art. Exemplary of such materials are strands or ribbons of a polymeric, elastomeric material which are adhered to the absorbent article 20 in a stretched position, or which are attached to the absorbent article while the article is pleated, such that elastic constrictive forces are imparted to the absorbent article 20. In a particular aspect of the invention, the elastics may be composed of individual strands of Lycra® which are available from E. I. DuPont de Nemours Co., a business having offices in Wilmington, Delaware. It should be noted that leg elastics 38 and waist elastics 40 and 42 are typically used in conventional absorbent articles to reduce leakage which is caused by the inadequacies of the conventional absorbent structures and materials. The need for leg elastics 38 and waist elastics 40 and 42 in the absorbent article of the present invention to help prevent leakage may be reduced due to the improved composite absorbent core 34.

The leg elastics 38 and waist elastics 40 and 42 may have any configuration which provides the desired performance. For example, the leg elastics 38 and waist elastics 40 and 42 may comprise a single strand of elastic material, or may comprise several parallel or non-parallel strands of elastic material. The leg elastics 38 may be generally straight or optionally curved to more closely fit the contours of the legs and buttocks of the wearer and better contain bodily exudates. The leg elastics 38 and waist elastics 40 and 42 may be attached to the absorbent article 20 in any of several ways which are well known to those skilled in the art. For example, the elastics may be ultrasonically bonded, thermally bonded or adhesively bonded to the absorbent article 20.

The fastening means 44 are typically applied to the corners of the rear portion 24 of the absorbent article 20 to provide a means for holding the article 20 on the wearer. Suitable fastening means 44 are well known to those skilled in the art and can include tape tab fasteners, hook and loop fasteners, mushroom and loop fasteners, snaps, pins, belts and the like, and combinations thereof. Typically, the fastening means 44 are configured to be refastenable. It should also be understood that it may be possible to dispense with the fastening means 44 in an absorbent article having a given design configuration.

The composite absorbent core 34, as representatively illustrated in FIGS. 1A–1C, is positioned between the bodyside liner 30 and the outer cover 32 to form the absorbent article 20. The composite absorbent core 34 is generally conformable and capable of absorbing and retaining body exudates. It should be understood that, for the purpose of the present invention, the composite absorbent core 34 may comprise a single, integral piece of material or, alternatively, may comprise a plurality of individual separate pieces of material which are operably assembled together. Where the composite absorbent core 34 comprises a single, integral piece of material, the material may include the desired structural features formed into selected spacial regions thereof. Where the composite absorbent core 34 comprises multiple pieces, the pieces may be configured as discrete layers or other nonlayered shapes and configurations. The pieces or layers may be coextensive or non-coextensive, depending upon the requirements of the absorbent article 20. It is preferred, however, that each of the pieces or layers be arranged in an operable, intimate contact with at least one other adjacent piece or layer of the absorbent article 20. Preferably, each piece or layer is connected to an adjacent portion of the absorbent article 20 by suitable bonding means, such as ultrasonic or adhesive bonding, or mechanical or hydraulic needling as are well known to those skilled in the art.

Figure 2:
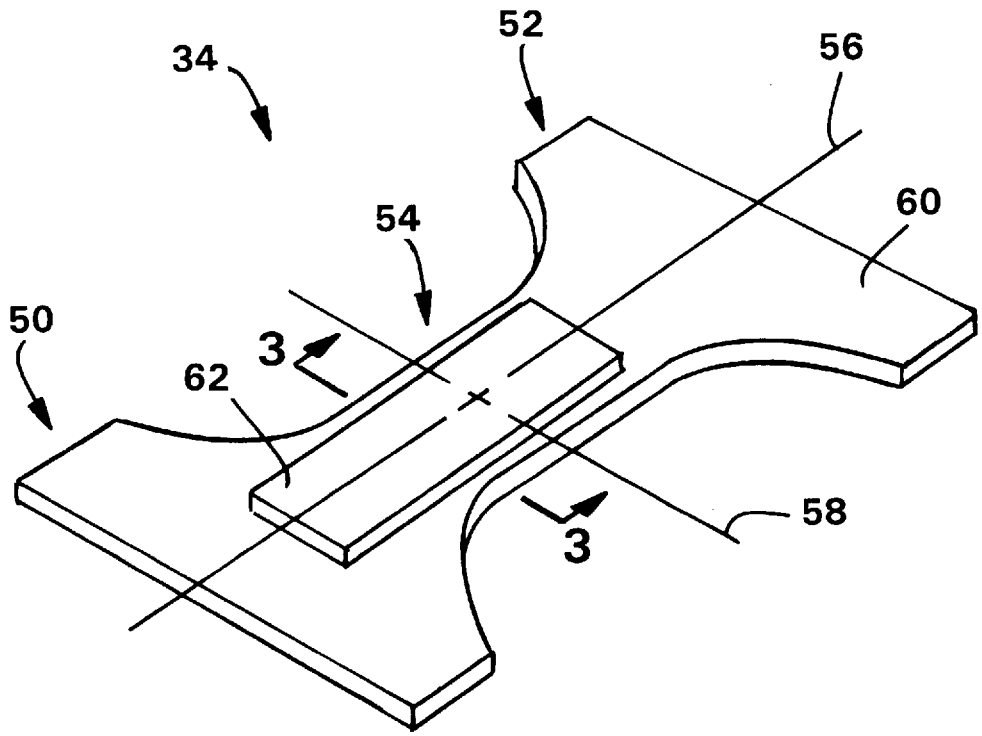
FIG. 2 representatively shows a perspective view of a composite absorbent core of the present invention.
Figure 3:
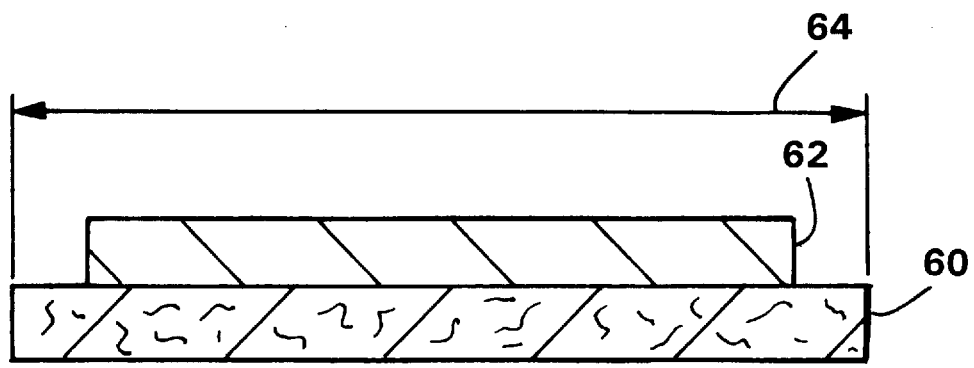
FIG. 3 representatively shows a lateral cross-sectional view of the absorbent core of FIG. 2 taken along line 3—3.

FIGS. 2 and 3 representatively illustrate one example of the composite absorbent core of the present invention. The composite absorbent core 34 has a front section 50, a back section 52, a crotch section 54, a longitudinal centerline 56 and a transverse centerline 58. The composite absorbent core 34 has two generally inwardly bowed lateral edges providing a narrow crotch width dimension 64 in the crotch section 54 for positioning between the legs of the wearer. When used in an absorbent article, such as the absorbent article 20 representatively illustrated in FIGS. 1A–1C, the front section 50, back section 52 and crotch section 54 of the composite absorbent core 34 are located in the front portion 22, back portion 24 and crotch portion 26 of the absorbent article 20, respectively. As representatively illustrated in FIGS. 2 and 3, the composite absorbent core 34 also has at least one absorbent portion 60 and at least one porous resilient portion 62.

The composite absorbent core 34 may have any of a number of shapes and sizes. For example, the composite absorbent core may be rectangular, I-shaped or T-shaped. The size and absorbent capacity of the composite absorbent core 34 should be compatible with the size of the intended wearer and the fluid loading imparted by the intended use of the absorbent article. In a particular aspect of the invention, the composite absorbent core 34 is designed to have an absorbent capacity of at least about 300 grams of synthetic urine and desirably at least about 400 grams of synthetic urine to provide improved performance. The absorbent capacity of the absorbent article 20 may be provided entirely by the composite absorbent core 34 or may be a greater amount depending upon the configuration of the various portions of the absorbent article 20. As used herein, the term "absorbent capacity" refers to the absorbent capacity value as determined according to the Absorbent Capacity Test as set forth in the TEST PROCEDURES section below.

It is generally preferred that the composite absorbent core 34 be narrower in the crotch section 54 of the absorbent core 34 than in the front or back section, 50 or 52, respectively. It has been found that the composite absorbent core 34 of the present invention is particularly useful when the crotch width dimension 64 of the crotch section 54 of the composite absorbent core 34 is from about 3.18 to about 6.35 centimeters (1.25 to about 2.50 inches), desirably no more than about 5.08 centimeters (2.00 inches) and more desirably no more than about 3.81 centimeters (1.50 inches). The narrow crotch width dimension 64 of the crotch section 54 of the composite absorbent core 34 allows the absorbent article 20 to correspondingly have a narrow overall crotch portion. For example, as representatively illustrated in FIGS. 1A–1C, the crotch portion 26 of the absorbent article may have an article crotch width dimension 48 which is from about 7.62 to about 22.86 centimeters (3.00 to about 9.00 inches), desirably no more than about 17.78 centimeters (7.00 inches) and more desirably no more than about 12.70 centimeters (5.00 inches). Such a narrow article crotch width provides for a better fitting and more aesthetically pleasing absorbent article.

The composite absorbent core 34 of the different aspects of the present invention may have a basis weight of from about 500 to about 1200 grams per square meter and desirably from about 700 to about 1000 grams per square meter for improved performance.

The absorbent portion 60 of the composite absorbent core 34 may suitably comprise various types of wettable, hydrophilic fibrous materials. Examples of suitable materials include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester and polyamide fibers; and synthetic fibers composed of a nonwettable thermoplastic polymer, such as polypropylene fibers, which have been hydrophilized by appropriate means known to those skilled in the art. The absorbent portion 60 may also comprise selected blends of the various types of fibers mentioned above.

In a particular aspect of the invention, the absorbent portion 60 of the composite absorbent core 34 may include a matrix of hydrophilic fibers, such as a web of cellulosic fibers, mixed with particles of a high-absorbency material such as that commonly known as superabsorbent material. As used herein, the term "high-absorbency material" refers to materials that are capable of absorbing at least 10 times their own weight in liquid. In a particular embodiment, the absorbent portion 60 comprises a mixture of superabsorbent hydrogel-forming particles and wood pulp fluff. The wood pulp fluff may be exchanged with synthetic, polymeric, meltblown fibers or with a combination of meltblown fibers and natural fibers. The high-absorbency material may be substantially homogeneously mixed with the hydrophilic fibers or may be nonuniformly mixed. The high-absorbency material may also be arranged in a generally discrete layer within the matrix of hydrophilic fibers. Alternatively, the absorbent portion 60 may comprise a laminate of fibrous webs and high-absorbency material or other suitable means of maintaining a high-absorbency material in a localized area.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystallined domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), polyvinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and w holly or partially synthetic absorbent polymers can also be useful in the present invention.

The high-absorbency material may be in any of a wide variety of geometric forms. As a general rule, it is preferred that the high-absorbency material be in the form of discrete particles. However, the high-absorbency material may also be in the form of fibers, flakes, rods, spheres, needles, or the like. Conglomerates of particles of high-absorbency material may also be used. An example of a superabsorbent polymer suitable for use in the present invention is a superabsorbent polymer designated IM5000 which is commercially available from Hoechst-Celanese, a business having offices in Portsmouth, Va.

Other suitable high-absorbency materials may include superabsorbent polymers which are commercially available from Dow Chemical Corp., a business having offices in Midland, Mich.

As a general rule, the high-absorbency material is present in the composite absorbent core 34 of the present invention in an amount of from about 5 to about 95 weight percent and desirably from about 25 to about 80 weight percent based on the total weight of the composite absorbent core 34. The distribution of the high-absorbency material within the different portions of the composite absorbent core 34 can vary depending upon the intended end use of the absorbent core 34.

In a particular aspect of the invention, the absorbent portion 60 comprises high-absorbency particles which are distributed within a matrix of cellulosic fibers or fluff at an amount of at least about 25 weight percent, desirably from about 30 to about 90 weight percent and more desirably from about 40 to about 80 weight percent based on the total weight of the absorbent portion 60 of the composite absorbent core 34. In addition, the absorbent portion 60 may have a density of from about 0.10 to about 0.40 grams per cubic centimeter and desirably from about 0.15 to about 0.35 grams per cubic centimeter. The absorbent portion 60 may also have a basis weight of from about 500 to about 900 grams per square meter and desirably from about 600 to about 800 grams per square meter. As used herein, the term "density" refers to the density of the sample material when measured under a load of 0.138 Newtons per square centimeter (0.2 pounds per square inch). The high-absorbency particles and cellulosic fibers may be placed in selected zones of the absorbent portion 60 depending upon the intended use of the absorbent article 20. For example, the high-absorbency particles may be selectively placed in the central region of the absorbent portion 60 to reduce the amount of high-absorbency particles near the side and end edges of the absorbent portion 60. Such an arrangement may provide better containment of the high-absorbency particles within the cellulosic fibers.

As representatively illustrated in FIGS. 2 and 3, the absorbent portion 60 may include from about 10 to about 22 grams of cellulosic fibers and desirably from about 17 to about 21 grams of cellulosic fibers to provide improved performance. The absorbent portion 60 may also include from about 4 to about 9 grams of high-absorbency particles and desirably from about 5 to about 9 grams of high-absorbency particles. The cellulosic fibers carry and position the high-absorbency particles within the composite absorbent core 34. A suitable amount of cellulosic fibers and high-absorbency particles are incorporated into the absorbent portion 60 such that the absorbent portion 60 provides a total absorbent capacity of from about 300 to about 600 and desirably at least about 400 grams of synthetic urine. In a particular aspect, the absorbent capacity of the composite absorbent core 34 is substantially provided by the absorbent portion 60.

As representatively illustrated in FIGS. 2 and 3, the composite absorbent core 34 of the present invention also contains a porous resilient portion 62 to advantageously provide sufficient void volume to improve the overall distribution of fluid within the composite absorbent core 34. The improved distribution more effectively utilizes the absorbent capacity of the composite absorbent core 34. The resilient portion 62 is typically less hydrophilic than the absorbent portion 60. The resilient portion 62 is also configured to provide resilient void volume to accept and distribute fluid surges to remote areas of the absorbent portion 60 even when subjected to compressive forces caused by the wearer's position and movement. The resilient portion 62 should be both dry resilient and wet resilient to maintain sufficient void volume even after initial fluid surges. The resilient void volume of the porous resilient portion 62 helps prevent fluid exudates from pooling and collecting on portions of the composite absorbent core 34 and is particularly useful in composite absorbent cores which have a very narrow crotch.

As representatively illustrated in FIGS. 2 and 3, the porous resilient portion 62 may be configured to be in fluid communication with the absorbent portion 60 of the composite absorbent core 34. In the illustrated embodiment, the porous resilient portion 62 comprises a discrete layer which is positioned over the absorbent portion 60. This configuration is particularly useful to receive discharged fluids in one location of the composite absorbent core 34 and quickly redistribute the fluids to other areas of the composite absorbent core 34.

The porous resilient portion 62 may be of any desired shape and configuration. Suitable shapes include, for example, circular, rectangular, triangular, trapezoidal, oblong, dog-boned, hourglass-shaped, or oval. Desirably, the shape of the porous resilient portion 62 provides a sufficient amount of surface area which is in fluid communication with the absorbent portion 60. The porous resilient portion 62 has a width which is generally from about 50 to about 150 percent and desirably from about 100 to about 125 percent of a width of the absorbent portion 60. The porous resilient portion 62 may also extend over the entire length of the composite absorbent core 34 or may only extend partially along the length of the composite absorbent core 34. When the porous resilient portion 62 is shorter in length than the absorbent core 34, the porous resilient portion 70 can be selectively positioned anywhere along the composite absorbent core 34. In a particular aspect of the invention, the porous resilient portion 62 is approximately centered about the longitudinal centerline 56 of the composite absorbent core 34 and positioned primarily in the front section 50 and crotch section 54 of the composite absorbent core 34.

Typically, fluid exudates are discharged into the crotch section 54 and a portion of the front section 50 nearest the transverse line 58 of the composite absorbent core 34. Conventional absorbent structures have become saturated in these areas and have thus tended to leak prematurely. The problem of premature leakage is even more acute when the crotch section of the absorbent structures becomes quite narrow. However, the porous resilient portion 62 of the composite absorbent core 34 of the present invention reduces the frequency of premature leakage by providing a means for the discharged fluid to immediately be distributed to other areas of the composite absorbent core 34, such as the region of the front section 50 of the absorbent core 34 furthest from the transverse line 58 of the absorbent core 34 and the back section 52 of the absorbent core 34.

Various materials can be used to construct the porous resilient portion 62. For example, the porous resilient portion 62 may be a nonwoven web of fibers, a foam, or any other suitable material which provides the desired function. The porous resilient portion 62 may be a substantially hydrophobic material and, optionally, can be treated with a surfactant or otherwise to impart a desired level of wettability and hydrophilicity.

If the porous resilient portion 62 is a foam material, any type of polymer which can be foamed and which can provide the desired function can be used. For example, the porous resilient material 62 may be an open-celled foam material made from polystyrene, polyvinylchloride, polyethylene, polyolefins, polyurethane, polyisocyanates, polyphenols, epoxy resins, silicon resins and the like. The foam material may also be rigid, semi-rigid or flexible. In a particular aspect of the invention, the porous resilient portion 62 is a semi-rigid, polyurethane open-celled foam material.

Methods of forming such foam materials are well known to those skilled in the art. As is well known to tho se skilled in the art, the physical properties of the resultant foam materials can be varied broadly by controlling the ingredients and processing of the foam materials. Following the foaming of the polymer, the structure of the foam can also be modified by processes known to those skilled in the art to provide a greater number of open cells in the cell structure. For example, the percentage of open cells in t he foam material can be increased to as great as 99 percent or higher. Foam materials having greater than 95 percent open cells are generally known as "reticulated" foams. Foam materials having an increased number of open cells are particularly desired for the porous resilient portion 62 of the composite absorbent core 34 of the present invention. In a particular aspect of the invention, the porous resilient portion 62 comprises a polyurethane foam material wherein at least 80 percent and desirably at least 95 percent of the cells present in the foam are open cells. For example, the porous resilient portion 62 may include a polyurethane foam material designated Style #80,000 Federal Foam which is commercially available from Illbruck, Inc. a business having offices located in Minneapolis, Minn.

In a particular aspect of the invention, the porous resilient portion 62 has a density (determined at a load of 0.2 psi) which is not more than about 0.050 grams per cubic centimeter and desirably from a bout 0.010 to about 0.030 grams per cubic centimeter to provide improved performance. Desirably, the porous resilient portion 62 also has a basis weight of from about 100 to about 200 grams per square meter and more desirably from about 125 to about 175 grams per square meter. Moreover, the porous resilient portion 62 is desirably substantially free of high-absorbency mate rial such as absorbent gelling material such that the porous resilient portion 62 does not retain high amounts of fluid.

The porous resilient portion 62 may also be configured to have a mean pore size of at least about 1.50 millimeters and desirably from about 2.0 to about 4.0 millimeters. If the mean pore size is too small, the rate of fluid intake may be too slow and the distribution of the fluids may not effectively use substantially the entire absorbent capacity of the composite absorbent core 34. The mean pore size can be determined according to any of various methods known to those skilled in the art. One such method is the Pore Size Test as set forth in the TEST PROCEDURES section below.

The porous resilient portion 62 of the composite absorbent core 34 of the present invention may also be configured to temporarily hold the discharged fluid to allow sufficient time for the absorbent portion 60 to absorb and contain the fluids. In the different aspects of the present invention it is desirable that the porous resilient portion 62 maintain sufficient void volume to effectively distribute and temporarily hold the discharged fluid. The void volume of the porous resilient portion 62 will vary as the load exerted upon it varies. It is particularly important that the porous resilient portion 62 be capable of maintaining a sufficient amount of void volume even when under load. As used herein, the term "void volume" refers to the void volume value as determined according to the void volume equation set forth in the Wet Compression Recovery Test in the TEST PROCEDURES section below.

In a particular aspect, the porous resilient portion 62 has a void volume which is at least about 20 cubic centimeters per gram and desirably from about 30 to about 50 cubic centimeters per gram when under no load. In addition, the composite absorbent core 34 can include a sufficient amount of the porous resilient portion 62 by weight to provide a void volume of at least about 3.0 cubic centimeters and desirably from about 5.0 to about 9.0 cubic centimeters under no load to provide improved performance. For example, the porous resilient portion 62 may include about 0.2 grams of a polyurethane foam material having a void volume (under no load) of about 36 cubic centimeters per gram to provide about 7.2 cubic centimeters of void volume when under no load. In a particular aspect, the composite absorbent core 34 of the present invention includes from about 5 to about 20 weight percent and desirably from about 10 to about 15 weight percent of the porous resilient portion 62 based on the total weight of the composite absorbent core 34 to provide improved performance.

The porous resilient portion 62 of the composite absorbent core 34 is also desirably both wet and dry resilient to preserve the void volume for successive fluid surges even after being compressed by the wearer. The resiliency of the porous resilient portion 62 may be represented by the ability of the material to recover it's original volume after being compressed. In a particular aspect, the porous resilient portion 62 has a wet compression recovery of at least about 85 percent, desirably from about 90 to about 100 percent and more desirably from about 95 to about 100 percent. As used herein, the term "wet compression recovery" refers to the compression recovery value determined according to the Wet Compression Recovery Test as set forth in the TEST PROCEDURES section below. It is also desirable that the porous resilient portion 62 maintain at least about 25 percent, desirably from about 30 to about 100 percent and even more desirably from about 50 to about 100 percent of it's void volume (under no load) when under a load of 0.673 Newtons per square centimeter (0.975 pounds per square inch).

Figure 4:
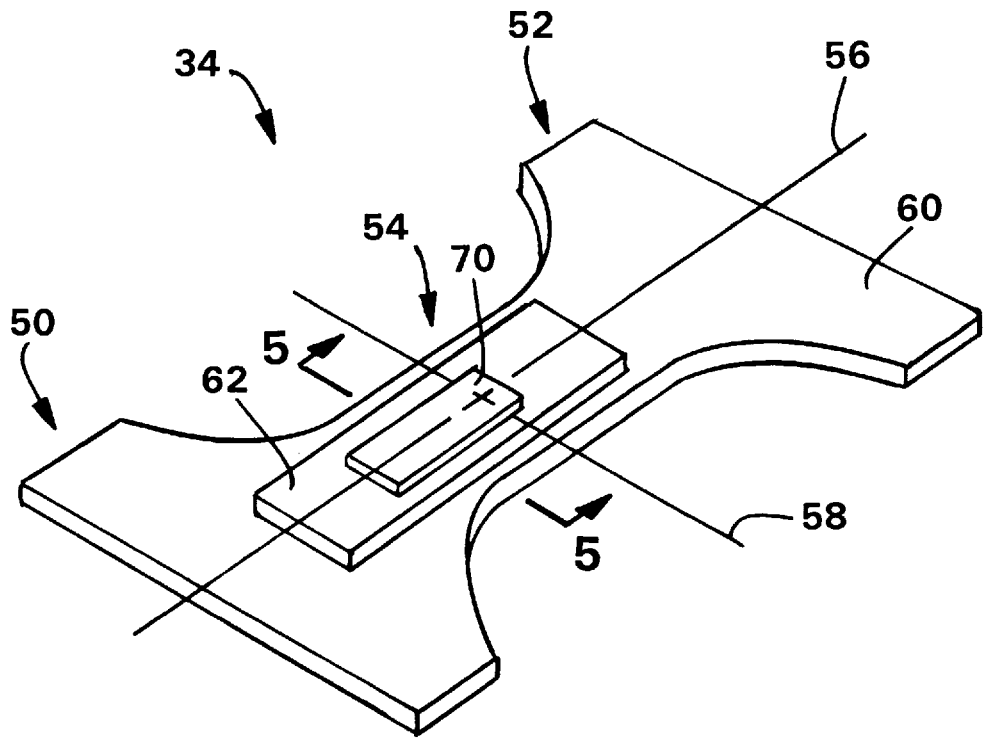
FIG. 4 representatively shows a perspective view of another composite absorbent core of the present invention.
Figure 5:
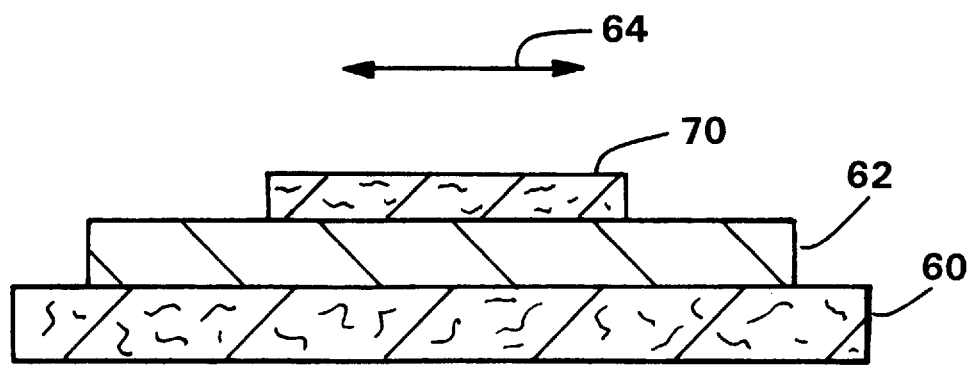
FIG. 5 representatively shows a lateral cross-sectional view of the absorbent core of FIG. 4 taken along line 5—5.

In another aspect of the invention as representatively illustrated in FIGS. 4 and 5, the composite absorbent core 34 of the present invention may also contain a surge portion 70 to advantageously improve the overall fluid intake rate of the composite absorbent core 34. The surge portion 70 is typically less hydrophilic than the absorbent portion 60 and is configured to collect and temporarily hold fluid surges. This configuration can also help prevent fluid exudates from pooling and collecting on portions of the composite absorbent core 34.

Various woven and nonwoven materials can be used to construct the surge portion 70. For example, the surge portion 70 may be a layer of a spunbonded or meltblown web of polyolefin fibers. The surge portion 70 may also be a bonded carded web of natural and synthetic fibers. The surge portion 70 may be a substantially hydrophobic material and, optionally, can be treated with a surfactant or otherwise to impart a desired level of wettability and hydrophilicity. In a particular aspect of the invention, the surge portion 70 has a density (determined at a load of 0.2 psi) which is not more than about 0.10 grams per cubic centimeter and desirably from about 0.04 to about 0.06 grams per cubic centimeter to provide improved performance. The surge portion 70 is substantially free of high-absorbency material such as absorbent gelling material such that the surge portion 70 does not retain high amounts of fluid. However, the surge portion 70 may contain small amounts of high-absorbency material to help acquire a fluid surge.

As representatively illustrated in FIGS. 4 and 5, the surge portion 70 may be configured to be in fluid communication with the absorbent portion 60 and the resilient portion 62 of the composite absorbent core 34. The surge portion 70 may or may not extend the full length of the composite absorbent core 34. In the illustrated embodiment, the surge portion 70 comprises a discrete layer which is positioned over the porous resilient portion 62. The surge portion 70 serves to quickly collect and temporarily hold discharged fluids and then to eventually release the fluids into the porous resilient portion 62 and absorbent portion 60.

The surge portion 70 may be configured to allow a controlled discharge of the liquid exudates such that the liquid exudates remain in the void volume of the surge portion 70 for a limited period of time. As such, the surge portion 70 may be configured to avoid allowing the liquid exudates to simply pass directly through or gush laterally along the plane of the surge portion 70. In a particular aspect of the invention, the surge portion 70 may be configured to have a mean pore size of from about 0.20 to about 1.00 millimeters and desirably from about 0.30 to about 0.90 millimeters as determined according to any of various methods known to those skilled in the art such as the Pore Size Test set forth in the TEST PROCEDURES section below. If the mean pore size is too small, the rate of fluid intake may be too slow and if the effective pore size is too large, the fluids may not be retained in the surge portion 70 for a sufficient amount of time to allow fluids to be effectively desorbed into the absorbent portion 60.

In the different aspects of the invention as representatively illustrated in FIGS. 4 and 5, the surge portion 70 can comprise a nonwoven material having a basis weight of from about 30 to about 240 grams per square meter and may contain bicomponent fibers. For example, the surge portion 70 may include a nonwoven fibrous web which includes about 60 weight percent polyester fibers, such as PET fibers which are commercially available from Hoechst-Celanese. Suitable bicomponent fibers include a wettable, polyethylene/polypropylene bicomponent fiber available from Chisso, Corp., a business having offices located in Osaka, Japan. The polyester fibers and bicomponent fibers are generally homogeneously bonded together. The surge portion 70 may also include other wettable fiber materials such as cotton, rayon, wood pulp, inherently wettable synthetic polymers, hydrophilized or surface treated polymers and the like.

The surge portion 70 may be of any desired shape and configuration. Suitable shapes include, for example, circular, rectangular, triangular, trapezoidal, oblong, dog-boned, hourglass-shaped, or oval. Desirably, the shape of the surge portion 70 provides a sufficient amount of surface area which is in fluid communication with the absorbent portion 60. The surge portion 70 has a width which is generally from about 50 to about 150 percent and desirably at least about 75 percent of the width of the absorbent portion 60 of the composite absorbent core 34. The surge portion 70 may also extend over the entire length of the composite absorbent core 34 or may only extend partially along the length of the composite absorbent core 34. When the surge portion 70 is shorter in length than the absorbent core 34, the surge portion 70 can be selectively positioned anywhere along the composite absorbent core 34. In a particular aspect of the invention, the surge portion 70 is approximately centered about the longitudinal centerline 56 of the composite absorbent core 34 and positioned primarily in the front section 50 and crotch section 54 of the composite absorbent core 34.

The different portions of the composite absorbent core 34 of the present invention may be selectively designed and configured such that a capillary force differential or gradient is created at the interface between each portion, such as between the absorbent portion 60 and the porous resilient portion 62. The capillary force differential can advantageously improve the performance of the composite absorbent core 34. For example, where the porous resilient portion 62 is positioned immediately adjacent the absorbent portion 60 and the porous resilient portion 62 is designed to have a lower capillary attraction as compared to the capillary attraction of the absorbent portion 60, then fluids will tend to be desorbed more readily from the porous resilient portion 62 into the absorbent portion 60. To provide the desired difference in capillary attraction, the porous resilient portion 62 may be configured to have a larger mean pore size than the mean pore size of the section of the absorbent portion 60 which is immediately adjacent the porous resilient portion 62. In addition, the porous resilient portion 62 can also be configured to be less hydrophilic than the absorbent portion 60.

The composite absorbent core 34 of the different aspects of the present invention may be comprised of any suitable combination of absorbent portions 60, porous resilient portions 62 and surge portions 70, as described above, to provide the desired effectiveness. The porous resilient portions 62 may include several different layers which more effectively distribute the discharged fluids to remote areas of the absorbent portion 60 of the composite absorbent core 34. For example, the porous resilient portions 62 may be arranged to provide a "cascading" effect on the discharged fluids to increase the displacement and distribution of the fluids along the planar surface of the absorbent portion 60.

Figure 6:
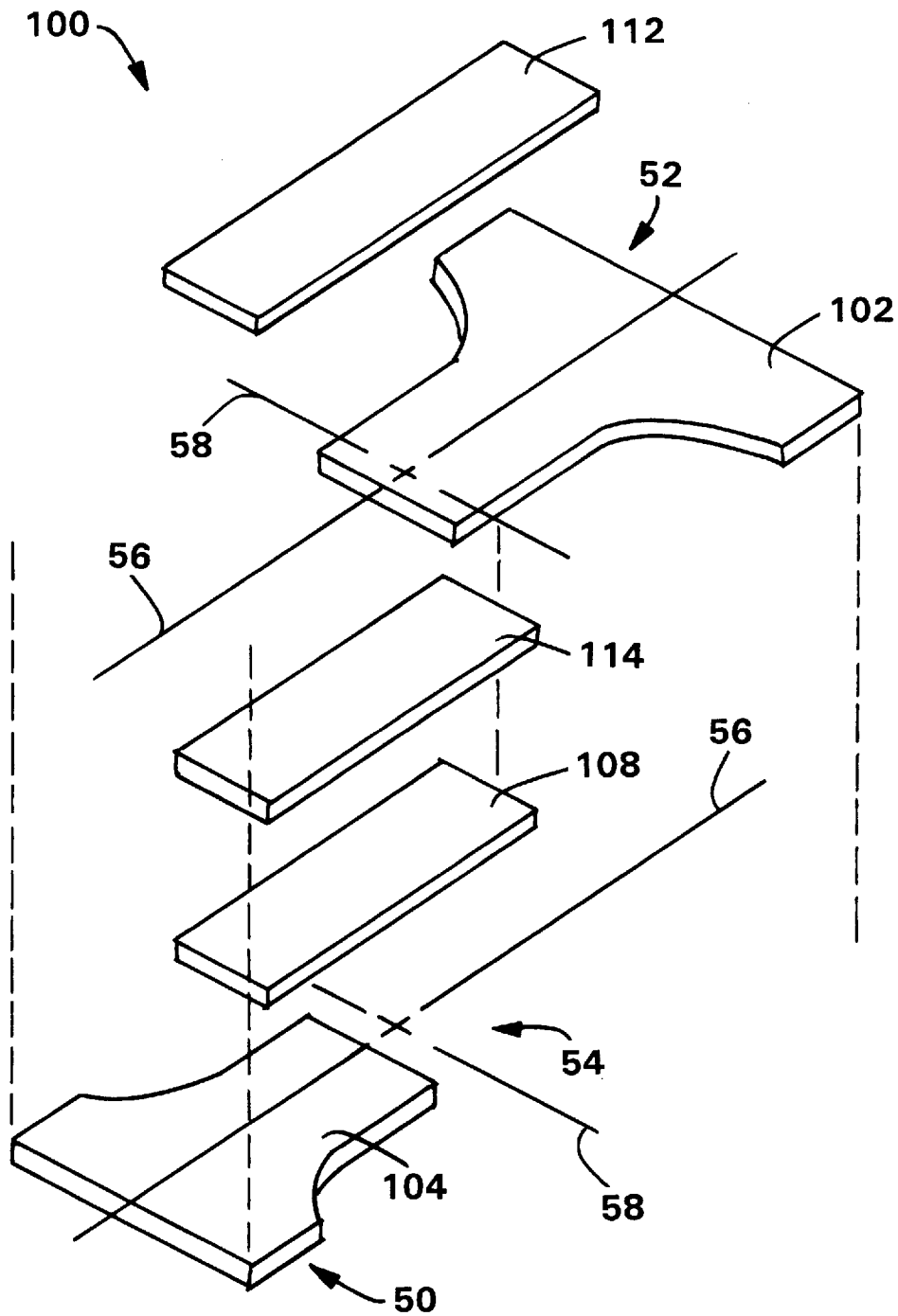
FIG. 6 representatively shows a perspective view of another composite absorbent core of the present invention.

FIG. 6 representatively illustrates another embodiment of the composite absorbent core of the present invention. As representatively illustrated in FIG. 6, the composite absorbent core 100 may have a front section 50, a back section 52, a crotch section 54, a longitudinal centerline 56 and a transverse centerline 58. The composite absorbent core 100 has two generally inwardly bowed lateral edges providing a narrow width in the crotch section 54 for positioning between the legs of the wearer. As representatively illustrated in FIG. 6, the composite absorbent core 100 includes an arrangement of absorbent portions, porous resilient portions and surge portions to provide improved performance. The absorbent portions, porous resilient portions and surge portions may be configured to be similar to the respective portions described above.

The various portions of the composite absorbent core 100 can be configured in any particular order which provides the desired performance in the absorbent article. In a particular aspect of the invention, as representatively illustrated in FIG. 6, the composite absorbent core 100 may include a first absorbent portion 102 and a second absorbent portion 104. A first porous resilient portion 108 may be positioned between the first absorbent portion 102 and the second absorbent portion 104 such that the first porous resilient portion 108 is in direct, fluid communication with at least one of the first and the second absorbent portions, 102 and 104 respectively. The first porous resilient portion 108 is configured to provide resilient void volume to accept and distribute fluid surges to remote areas of both the first and the second absorbent portions 102 and 104.

The absorbent portions 102 and 104 and the porous resilient portion 108 may be provided by any of the materials discussed above and may be any shape or size which provides the desired performance. Each of the different portions need not extend the entire length and width of the composite absorbent core 100. For example, as representatively illustrated in FIG. 6, the first absorbent portion 102 may selectively be disposed in the back section 52 and crotch section 54 of the composite absorbent core 100 while the second absorbent portion may be disposed in the front section 50 of the composite absorbent core 100. In this configuration, the first porous resilient portion 108 may comprise a layer which extends between the first and second absorbent portions 102 and 104 and may or may not extend along the entire length and width of the composite absorbent core 100.

In a particular aspect, the composite absorbent core 100 may further include at least one surge portion to advantageously improve the overall fluid intake rate of the composite absorbent core 100. For example, as representatively illustrated in FIG. 6, the composite absorbent core 100 may include a first surge portion 112 which is positioned in direct fluid communication with the first absorbent portion 102. The composite absorbent core 100 may further include a second surge portion 114 which extends generally between the first and second absorbent portions 102 and 104 and is in direct fluid communication with at least one of the absorbent portions 102 and 104.

Figure 7:
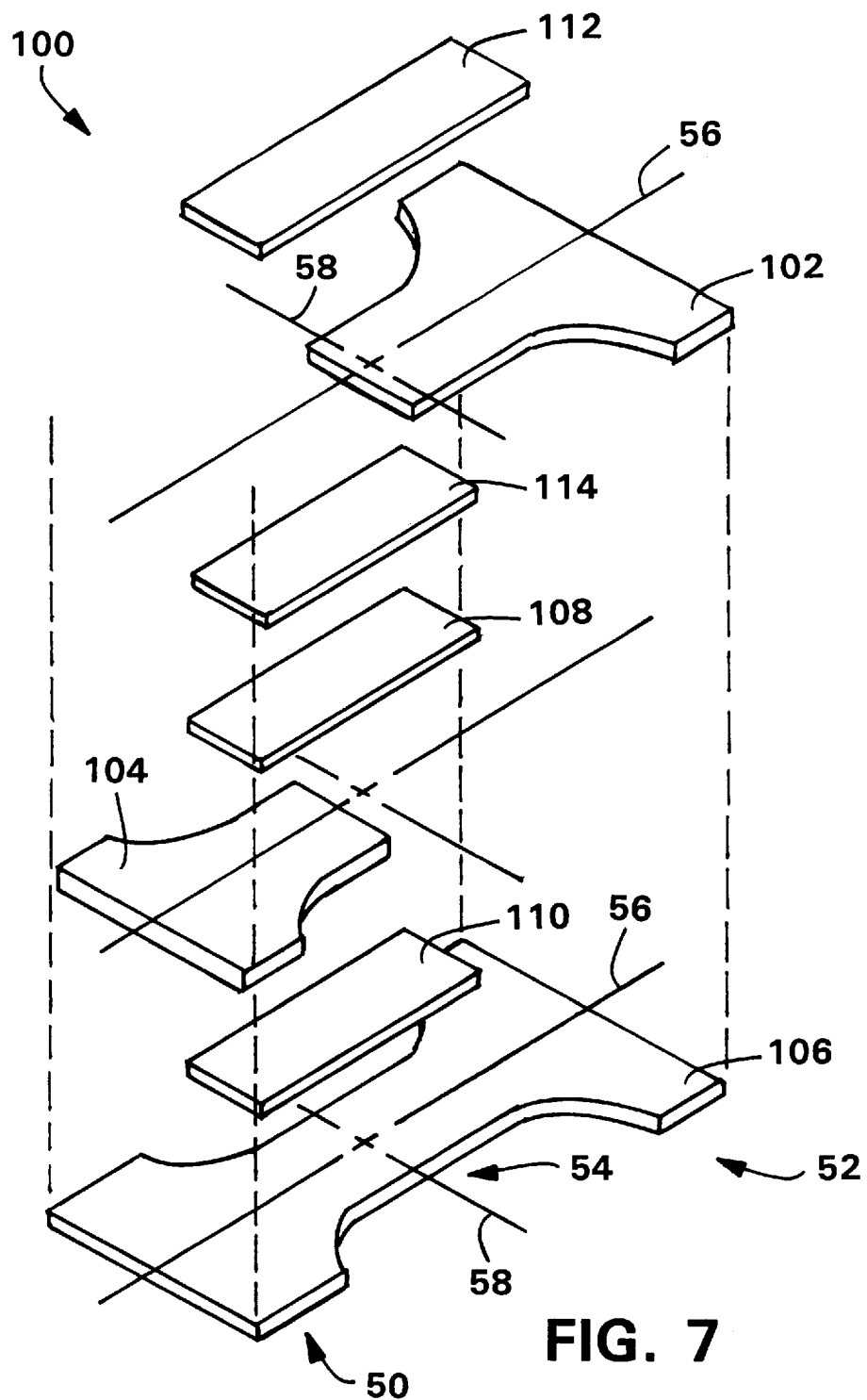
FIG. 7 representatively shows a perspective view of another composite absorbent core of the present invention.

FIG. 7 representatively illustrates another embodiment of the composite absorbent core of the present invention. As representatively illustrated in FIG. 7, the composite absorbent core 100 may include a first absorbent portion 102, a second absorbent portion 104 and a third absorbent portion 106. A first porous resilient portion 108 may be positioned between the first absorbent portion 102 and the second absorbent portion 104 such that the first porous resilient portion 108 is in direct, fluid communication with at least one of the first and the second absorbent portions, 102 and 104 respectively. A second porous resilient portion 110 may be positioned between the second absorbent portion 104 and the third absorbent portion 106 such that the second porous resilient portion 110 is in direct, fluid communication with at least one of the second and the third absorbent portions, 104 and 106 respectively. The first and second porous resilient portions 108 and 110 are configured to provide resilient void volume to accept and distribute fluid surges to remote areas of the first, second and third absorbent portions 102, 104 and 106.

The absorbent portions 102, 104 and 106 and the porous resilient portions 108 and 110 may be provided by any of the materials discussed above and may be any shape or size which provides the desired performance. Each of the different portions need not extend the entire length and width of the composite absorbent core 100. For example, as representatively illustrated in FIG. 7, the first absorbent portion 102 may selectively be disposed in the back section 52 and crotch section 54 of the composite absorbent core 100 while the second absorbent portion may be selectively disposed in the front section 50 of the composite absorbent core 100. In this configuration, the first porous resilient portion 108 may comprise a layer which extends between the first and second absorbent portions 102 and 104 and may or may not extend along the entire length and width of the composite absorbent core 100. The third absorbent portion 106 may be located underneath the first and second absorbent portions 102 and 104 and may extend substantially along the entire length of the composite absorbent core 100. The second porous resilient portion 110 may comprise a layer which extends between the second and third absorbent portions 104 and 106 and may or may not extend along the entire length and width of the composite absorbent core 100.

The composite absorbent core 100 as representatively illustrated in FIG. 7 may further include a first surge portion 112 and a second surge portion 114 to advantageously improve the overall fluid intake rate of the composite absorbent core 100. For example, the first surge portion 112 may be positioned in direct fluid communication with the first absorbent portion 102 and the second surge portion 114 may be in direct fluid communication with at least one of the first, second or third absorbent portions 102, 104 or 106.

It should be understood that the characteristics of each of the similar portions, such as the porous resilient portions, may differ when there are more than one of the similar portions. For example, as representatively illustrated in FIG. 7, the first porous resilient layer 108 may have a lower density than the second porous resilient layer 110.

It has been found that a composite absorbent core having several different portions or layers, as representatively illustrated in FIGS. 6 and 7, provides improved distribution of fluid exudates to remote areas of the absorbent portions, such as absorbent portions 102 and 104. The porous resilient portions tend to quickly and evenly distribute the discharged fluids and provide resilient void volume while the surge portions enhance the overall fluid intake rate of the composite absorbent core 100. The fluid exudates tend to be distributed by a "cascading" effect from one portion to the next. As opposed to conventional absorbent structures which typically have one path for the fluid to travel, the different portions of the composite absorbent core 100 provide several different paths for the fluids to travel before they are absorbed by the absorbent portions. The number and complexity of the different paths along which the fluids can travel is dependent upon the number and type or function of the different portions incorporated into the composite absorbent core.

For example, in the composite absorbent core 100 representatively illustrated in FIG. 6, the discharged fluids may enter the absorbent core 100 at the first surge portion 112. The fluids may then pass through the first surge portion 112 directly into the first absorbent portion 102, into the second surge portion 114, or into the first porous resilient portion 108. The portion of the fluids transferred into the second surge portion 114 may then be transferred along the second surge portion 114 and into the first absorbent portion 102 or, optionally, may pass into the first porous resilient portion 108 or into the second absorbent portion 104. Any fluids transferred into the porous resilient portion 108 may then be absorbed by either the first or the second absorbent portions 102 and 104.

The relative shape, longitudinal placement and arrangement of the different portions of the composite absorbent core of the different aspects of the present invention can be selected to provide the best performance depending upon the size, age and gender of the wearer. The location of the discharge of liquid body exudates from the wearer can vary widely for the different categories of wearers. For example, male infants tend to urinate towards the front portion of diaper articles while female infants tend to urinate closer to the crotch portion of diaper articles. Thus, the different portions of the composite absorbent core 34 of the present invention can be arranged in many different configurations depending upon the typical urination location of the category of wearer.

The different configuration and properties of the different portions of the composite absorbent core of the present invention as representatively illustrated in FIGS. 2–7, are designed to provide an improved fluid intake rate. As used herein, the term "fluid intake rate" refers to the fluid intake rate as determined using the Forced Fluid Intake Test described below in the TEST PROCEDURES section. The different portions of the composite absorbent core provide sufficient void volume and distribution channels to effectively hold fluid discharges and distribute them to remote areas of the composite absorbent core thereby increasing the fluid intake rate while reducing leakage. In a particular aspect, the composite absorbent core and the absorbent article of the present invention are configured to have a fluid intake rate of at least about 10 milliliters per second, desirably from about 10 to about 40 milliliters per second, more desirably from about 20 to about 40 milliliters per second and most desirably at least about 25 milliliters per second to provide improved performance.

The different aspects of the present invention can advantageously provide an absorbent article having a resilient composite absorbent core which has a relatively narrow crotch width and is capable of efficiently distributing fluids to more effectively utilize the absorbent capacity of the absorbent article. The absorbent article can provide a conforming, comfortable fit about the wearer while sufficiently containing body exudates. As a result, the absorbent article of the present invention can reduce the amount of leakage around the leg openings of the absorbent article even when the width of the crotch section of the absorbent article is very narrow.

TEST PROCEDURES

Absorbent Capacity Test

The absorbent capacity test measures the amount of fluid which is retained in an absorbent article, such as a diaper, or an absorbent core after the article or core is loaded with an amount of fluid and an external pressure is applied.

Equipment & Materials

1. Saturated Capacity (SAT CAP) Tester with Magnehelic vacuum gage and latex dam; Tester is described in the Forced Intake and Flowback Evaluation (FIFE) test described in U.S. Pat. No. 5,192,606 which issued Mar. 9, 1993, to Proxmire et al.
2. Latex dam, 0.014 inch; Obtain from McMaster-Carr Supply Co., Chicago, Ill. 60680-4355.
3. Teflon coated mesh, ¼ inch mesh; Obtain from Eagle Supply and Plastic, Inc., Appleton, Wis. 54911.
4. Fiberglass screen, mesh size 18 per inch ×16 per inch; Obtain from a hardware store.
5. Synthetic Urine; such as synthetic urine available from PPG Industries, Appleton, Wis.
6. Saturation Tub to hold the sample to be tested.
7. Dry rack, flat, non-corroding of appropriate dimensions to hold the sample to be tested.
8. Balance, 2000 gram capacity and readable to 0.1 gram.
9. Textile Saw for cutting absorbent core samples.
10. Scissors
11. Timer, readable to one second.
12. Room with standard-condition atmosphere; Temperature=23+1° C. (73.4+1.8° F.) and Relative Humidity=50+2%.

Absorbent Core Only

Specimen Preparation

1. Cut the samples to 4×4 inches.
2. Weigh each sample to the nearest 0.1 gram and record the weight on the data sheet.

Testing Procedure

1. Fill the Saturation Tub with the synthetic urine to a minimum depth of 2 inches (51 millimeters).
2. Place the screen on the rack.
3. Place the samples on the screen at least one inch (25 millimeters) apart and submerge the rack and samples in the synthetic urine.
4. Saturate the samples for a minimum of 20 minutes, but not to exceed 20 minutes and 15 seconds.
5. After the samples are saturated, remove the rack, screen and samples from the synthetic urine.
6. Place the screen with the samples on the Saturated Capacity Tester. Allow to drip for one minute, then cover the samples with the latex dam and adjust the vacuum to 0.5 psi (13.8 inches of water). Hold at this pressure for five minutes.
7. After the five minutes, immediately remove the latex dam from the samples and remove the samples from the screen. Weigh the samples to the nearest 0.1 gram.
8. The Absorbent Capacity of the each sample is then calculated thus: Absorbent Capacity=Wet weight—Dry weight Absorbent Article Specimen Preparation 1. Weigh the article to the nearest 0.1 gram and record on the data sheet.
2. Cut the elastics on the article to allow it to lie flat.

Testing Procedure

1. Fill the Saturation Tub with the synthetic urine to a minimum depth of 2 inches (51 millimeters).
2. Place the screen on the rack.
3. Place the article on the screen with the poly side up and submerge the rack and article in the synthetic urine.
4. Saturate the article for a minimum of 20 minutes, but not to exceed 20 minutes and 15 seconds.
5. After the article is saturated, remove the rack, screen and article from the synthetic urine.
6. Place the screen with the article on the Saturated Capacity Tester. Allow to drip for one minute, then cover the article with the latex dam and adjust the vacuum to 0.5 psi (13.8 inches of water). Hold at this pressure for five minutes.
7. After the five minutes, immediately remove the latex dam from the article and remove the article from the screen. Weigh the article to the nearest 0.1 gram.
8. The Absorbent Capacity of the article is then calculated thus: Absorbent Capacity=Wet weight—Dry weight Wet Compression Recovery Test This test has been designed to measure the compression recovery of a material when it is wet. The wet compression recovery indicates the ability of a material to recover to its original volume after being subjected to a compressing force. Wet compression recovery is determined from void volume measurements and is measured using an INSTRON or SINTECH tensile tester which measures the resisting force as a material is compressed between a movable platen and a fixed base at a constant rate using a certain amount of force and subsequently releasing the force at the same rate.

Suitable equipment for this test could include:

Compression tester:

INSTRON model 6021 with compression test software and 1 kN load cell made by Instron of Bucks, England.

Balance:

Mettler of Highstown, N.J., model PM4600

Preferably pressure, or force, and platen position are recorded. If only force is recorded, pressure is calculated using:

$$P = \frac{F}{A_p} \cdot 10{,}000 \text{ cm}^2/\text{m}^2$$

where:

P=pressure in Pascals

F=force pushing back on the platen in Newtons $A_p$=area of the platen in square centimeters (18.9 cm$^2$)

Void volume for a given material is calculated as follows:

$$VV = \frac{Vol}{M} - \frac{1}{p_{fiber}}$$

where:

VV=void volume of the material sample in cubic centimeters per gram

Vol=volume of the material sample in cubic centimeters

M=mass of the material sample in grams $P_{fiber}$=fiber density in grams per cubic centimeter For materials made with multiple fiber types, the material fiber density is the weight average of each individual fiber density:

$$P_{fiber,\ Total} = \text{Wt } \%_{fiber\ 1} \cdot P_{fiber\ 1} + \text{Wt } \%_{fiber\ 2} \cdot P_{fiber\ 2} +$$

where:

wt %=weight percent of the fiber type in the material or $$\text{wt } \% = \frac{\text{fiber weight in composition}}{\text{total composition weight}} \times 100\%$$

When a foam material is being measured, $p_{fiber}$ is the density of the material from which the foam is fabricated. For example, if the foam material is a polyurethane foam, $p_{fiber}$ is the density of polyurethane. For foam materials, the void volume (VV) calculated using the preceding equation is an approximation and the actual void volume will become less than the calculated void volume (VV) as the number of closed cells within the foam material increases.

The void volume of a material will vary as the load upon the material varies. The void volume of the material for a given platen position is calculated using the void volume equation set forth above wherein:

Vol=$(x_o - x) \cdot A_m \cdot 0.1$ cm/mm where:

Vol=volume of material in cubic centimeters $X_o$=initial platen position from the base in millimeters x=platen position from initial position in millimeters $A_m$=area of sample material in square centimeters The base must be larger in size than the platen. Zero height between platen and base distance was set by bringing the platen down until it barely touches the base. The platen was then raised to the desired initial height from the zero distance. The initial platen position must be greater than the initial thickness of the sample material so that the test starts out at zero pressure on the sample. The sample material can be the same size as the platen or larger.

For the purpose of measuring wet void volume for the present specification, a 4.9 cm diameter circular platen was used to compress materials against the base at a rate of 5.08 mm/min up to a 1.32 kg load (6,900 Pascal or 1.00 lb/in$^2$ pressure). The platen was then returned at the same rate to the initial starting position. The initial starting position for the platen was the sample material thickness plus 1 mm from the base. Material samples were cut to 50.4 mm diameter circles and were tested in the center. Force and position data were recorded at uniform periods of time between 0.05 and 0.01 minutes. The test is run on five material samples and the results averaged.

Wet void volume was measured when the material sample was completely immersed in 0.9% aqueous saline throughout the test. A flat bottomed container such as a hexagonal polystyrene weighing dish catalog #02-202D from Fischer Scientific of Pittsburgh, Pa. was placed on the base and the platen was zeroed and set to the initial position as described above. A 0.9% aqueous saline solution was added to the container to fill it to a level just to the bottom of the platen at its initial position. An appropriate saline could be S/P certified blood bank saline made by Stephens Scientific of Riverdale, N.J. and distributed by Baxter Healthcare of McGraw Park, Ill. under catalog #B3158-1. For the purpose of measuring void volume for the present specifications, 120 ml of saline was placed in the container and the platen was initially set a distance equal to 1 mm greater than the thickness of the test material sample from the base.

The load cell was tared with this level of fluid in the container. The sample was placed in the fluid, under the platen and the test was then performed as described above. Buoyant force was found to have a negligible effect on pressure but if so desired it can be subtracted from the pressure readings at each platen position using the following equation:

$$P_B = p_{saline} \cdot g \cdot (x_o - x) \cdot \left| \frac{A_p}{A_d - A_p} + 1 \right| \cdot 0.01$$

where:

$P_B$=Pressure from buoyant force in Pascals $P_{saline}$=saline (fluid) density in grams per cubic centimeter $A_p$=area of the platen in square centimeters (18.9 cm$^2$)

Figure 8:
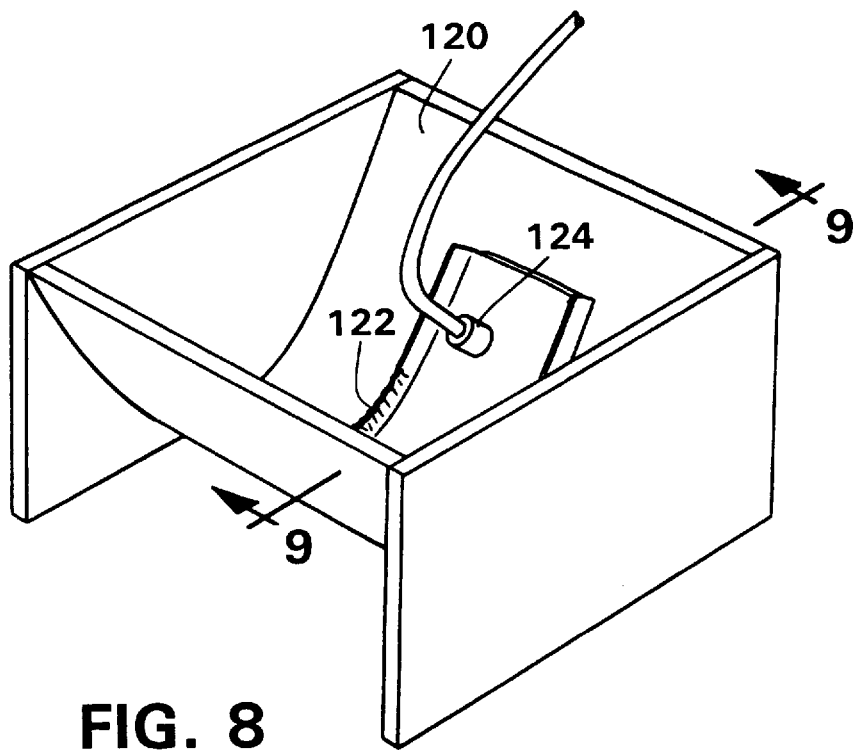
FIG. 8 representatively shows a perspective view of a testing apparatus used to evaluate the fluid intake rate of the composite absorbent cores and absorbent articles described herein.
Figure 9:
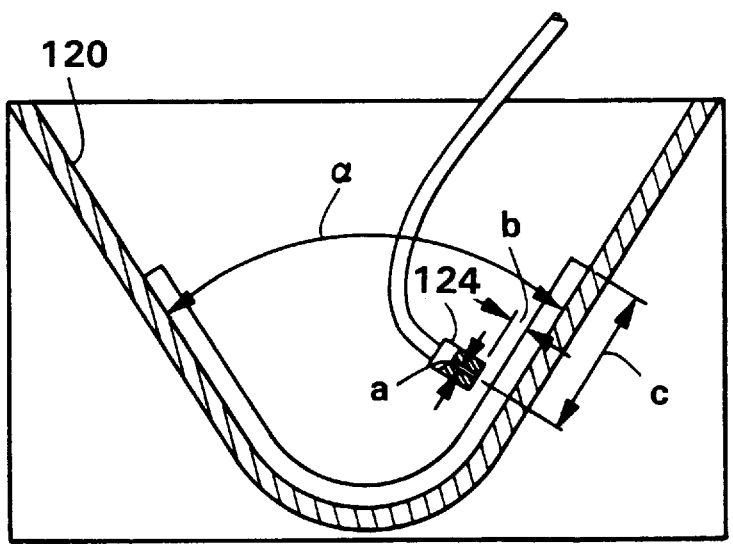
FIG. 9 representatively shows a cross-sectional view of the testing apparatus of FIG. 8.

$A_d$=area of the dish in square centimeters $X_o$=initial platen position from the base in millimeters x=platen position in millimeters g=standard acceleration of gravity which is 981 cm/seconds$^2$ 0.01=conversion factor=0.1 cm/mm·0.001 kg/gm·100 cm/m The overall pressure on the sample becomes:

$$P_{sample} = P_{reading} - P_B$$

where:

$P_{sample}$=pressure on the sample from the platen in Pascal $P_{reading}$=pressure reading from the SINTECH or INSTRON in Pascal $P_B$=buoyancy pressure from the 0.9% saline in Pascal Wet compression recovery was calculated using the platen positions on initial compression to 68.9 Pascal and on recovery when the pressure was equal to 68.9 Pascal:

$$\% \text{ Wet Compression Recovery} = \frac{VV_{recovery\,68.9Pa}}{VV_{compress\,68.9Pa}} \times 100$$

where:

$VV_{recovery\ 68.9\ Pa}$=void volume upon recovery at 68.9 Pascal pressure $VV_{compress\ 68.9\ Pa}$=void volume upon initial compression to 68.9 Pascal pressure Forced Fluid Intake Test The apparatus shown in FIGS. 8 and 9 is utilized for this test. This test has been designed to measure the fluid intake rate of an absorbent core or an absorbent article, such as an infant diaper. The fluid intake rate is measured by using a stop watch and visually determining the length of time required to absorb simulated urine voidings. The absorbent article is prepared by cutting the leg, waist and containment flap elastic members every 1" along their length in order to allow the sample to lie flat. The absorbent core of the sample may be tested either alone or within the absorbent article.

The sample to be tested is placed in a trough 120 which has an included angle, alpha, of 60° such that all of the test liquid is contained within the sample 122 by suitable dams placed along the edges of the sample. A specified amount of fluid (80 ml) is delivered from a nozzle 124 having a diameter of 4 millimeters. The fluid is a blood bank saline which is commercially available under the trade designation Baxter from Stephens Scientific, Inc., a business having offices located in Riverdale, N.J. The nozzle 124 is attached to a peristaltic pump equipped with a pulse suppressor. The nozzle 124 is placed a distance (b) of 6 millimeters from the sample 122 at a distance (c) about 4.5 centimeters from the end of the sample and at a perpendicular angle. The fluid is delivered at an average rate of 26.7 ml/sec for 3 seconds during each of three insults (80 ml per insult).

The time elapsing between the first fluid contact with the sample and the time when the fluid disappears into the sample is measured with a stop watch for each insult. The samples are allowed to equilibrate 15 minutes between insults. The fluid volume per insult (80 ml) is divided by the time elapsed between initial fluid contact and disappearance beneath the surface of the sample to determine the fluid intake rate for each insult in milliliters per second.

Pore Size Test

This test has been designed to measure the mean pore size of a sample of material which may be used in an absorbent article, such as an infant diaper. The sample of material has a thickness of about 0.25 inches (0.64 centimeters), a width of about 2.0 inches (5.1 centimeters), and a length of about 2.5 inches (6.35 centimeters). The sample is placed on a glass microslide having a width of 2.0 inches (5.1 centimeters) and a length of 3.0 inches (7.62 centimeters). The surface of the sample is coated with a 2:1 diluted solution of Pentel® Correction Fluid and isopropyl alcohol. The Pentel® Correction Fluid is commercially available from Pentel Co., Ltd., a business having offices located in Japan. The diluted solution migrates through the sample and is allowed to dry. The drying solution cements the sample to the glass microslide.

The microslide having the dried, coated sample adhered thereon is placed on a macroviewer stand and viewed through a 50 MM El-Nikkor f/2.8 enlarging lens. Lighting is provided by an 8-bulb octagonal ring illuminator that surrounds the lens to provide "incident darkfield" conditions. The mean pore size of the sample of material is determined using a Quantimet 970 Image Analyzer which is commercially available from Leica Instruments, Inc., a business having offices located in Deerfield, Ill. Major cut polygons and minor window faces are selected manually with a "light pen" when they are approximately orthogonal to the viewing plane. A program was developed to analyze the individual measurements and organize them into a histogram showing the total number of pores, the mean pore size and the standard deviation of the pore size.

EXAMPLES

The following examples are presented to provide a more detailed understanding of the invention. The particular materials and parameters are exemplary and are not intended to limit the scope of the invention.

EXAMPLE 1

A medium size diaper suitable for an infant weighing about 13–23 lbs. comprised a 1 mil thick outer cover composed of polyethylene film, a composite absorbent core of the present invention, and a bodyside liner composed of a spunbonded material. The bodyside liner was a nonwoven, spunbond, polypropylene fabric composed of about 2.8–3.2 denier fibers formed into a web having a basis weight of about 22 grams per square meter and a density of about 0.06 grams per cubic centimeter. The bodyside liner was surface treated with about 0.28 weight percent of a surfactant commercially available from Rohm and Haas Co. under the trade designation Triton X-102.

The composite absorbent core was arranged according to the configuration representatively illustrated in FIG. 7 and sandwiched between the outer cover and bodyside liner. The first absorbent portion 102 included about 6.4 grams of wood pulp fluff and 3.4 grams of a high-absorbency material. The first absorbent portion had a basis weight of 640 grams per square meter and covered an area of 153 square centimeters (23.75 square inches). The high-absorbency material was commercially available from Hoechst-Celanese under the trade designation IM5000. The second absorbent portion 104 included about 3.0 grams of wood pulp fluff and 1.0 grams of the IM5000 high-absorbency material. The second absorbent portion had a basis weight of 310 grams per square meter and covered an area of 129 square centimeters (20.0 square inches). The third absorbent portion 106 included about 6.75 grams of wood pulp fluff and 2.25 grams of the IM5000 high-absorbency material. The third absorbent portion had a basis weight of 310 grams per square meter and covered an area of 290 square centimeters (45.0 square inches).

The first and second porous resilient portions 108 and 110 were composed of a polyurethane foam material (Material A) which is commercially available under the trade designation Style #80,000 Federal Foam from Illbruck, Inc. The first porous resilient portion had a length dimension of 15.2 centimeters (6.0 inches) and a width dimension of 5.1 centimeters (2.0 inches) while the second porous resilient portion had a length dimension of 20.3 centimeters (8.0 inches) and a width dimension of 5.1 centimeters (2.0 inches).

To determine the wet compression recovery of the first and second porous resilient portions, five samples of the polyurethane foam material (Material A) were placed in an excess of saline (0.9 weight percent solution of sodium chloride in distilled water) and tested according to the Wet Compression Recovery Test as described above. The samples were 5 millimeters thick, had a basis weight of 160 grams per square meter and a density of 0.027 grams per cubic centimeter. The samples also had a mean pore size of 2.50 millimeters. The wet foam samples had an average pre-compression and post-compression void volume of 32.29 and 31.32 cubic centimeters per gram and a wet compression recovery of 97.0 percent. The results are also tabulated in Table 1 wherein the samples are designated Material A. As used herein the term "average" refers to the sum of the tested value for two or more samples divided by the total number of samples.

For comparative purposes, two other typical surge materials, Comparative Material A and Comparative Material B, were tested according to the Wet Compression Recovery Test as described above. Five samples of a first through-air bonded carded web surge material (Comparative Material A) were placed in an excess of saline (0.9 weight percent solution of sodium chloride and distilled water) and tested according to the Wet Compression Recovery Test as described above. The first surge material had a basis weight of 80 grams per square meter. The first surge material included 60 weight percent polyester fibers having a denier of about 6,35 weight percent polyethylene/polypropylene bicomponent fibers having a denier of about 2, and 5 weight percent high bulk polyethylene/polypropylene bicomponent fibers. The polyester fibers were PET (polyethylene terephthalate) type 295 fibers available from Hoechst-Celanese and the polyethylene/polypropylene bicomponent fibers were purchased from Chisso Corp., a business having offices in Osaka, Japan. The wet surge material samples had an average pre-compression and post-compression void volume of 53.04 and 39.10 cubic centimeters per gram and a wet compression recovery of 73.7 percent. The results are also tabulated in Table 1.

Five samples of a second through-air bonded carded web surge material (Comparative Material B) were also placed in an excess of saline (0.9 weight percent solution of sodium chloride and distilled water) and tested according to the Wet Compression Recovery Test as described above. The second surge material had a basis weight of 150 grams per square meter. The second surge material included 50 weight percent polyethylene/PET sheath-core bicomponent fibers having a denier of about 10 and 50 weight percent polyethylene/PET sheath-core bicomponent fibers having a denier of about 3. The polyethylene\PET sheath-core bicomponent fibers were purchased from BASF, a business having offices located in Ludwigshafen, Germany. The second surge material samples also had a mean pore size of 0.740 millimeters. The wet bicomponent surge material samples had an average pre-compression and post-compression void volume of 37.29 and 32.48 cubic centimeters per gram and a wet compression recovery of 87.1 percent. The results are also tabulated in Table 1.

TABLE 1

|  | Load (N/cm$^2$) | Void Volume (cm$^3$/g) Wet | Compression Recovery Wet |
|---|---|---|---|
| Material A | .007 | 32.29 |  |
|  | .673 | 11.68 | 97.0% |
|  | .007 | 31.32 |  |
| Comparative | .007 | 53.04 |  |
| Material A | .673 | 10.85 | 73.7% |
|  | .007 | 39.10 |  |
| Comparative | .007 | 37.29 |  |
| Material B | .673 | 16.13 | 87.1% |
|  | .007 | 32.48 |  |

As shown in Table 1, which illustrates the data obtained comparing Material A with Comparative Materials A and B, the polyurethane foam material (Material A) which can be used to provide the porous resilient portion of the different aspects of the present invention has an improved wet compression recovery when compared to typical surge materials.

The first surge portion 112 and second surge portion 114 were similar to Comparative Material A as described above except that they had a basis weight of 150 grams per square centimeter. The first surge portion 112 and second surge portion 114 also had a length dimension of 15.2 centimeters (6.0 inches) and a width dimension of 5.1 centimeters (2.0 inches). The porous resilient portions and surge portions were substantially centered about the longitudinal centerline 56 and transverse centerline 58 of the composite absorbent core. The composite absorbent core had a narrow crotch width dimension of 3.18 centimeters (1.25 inches).

Figure 10:
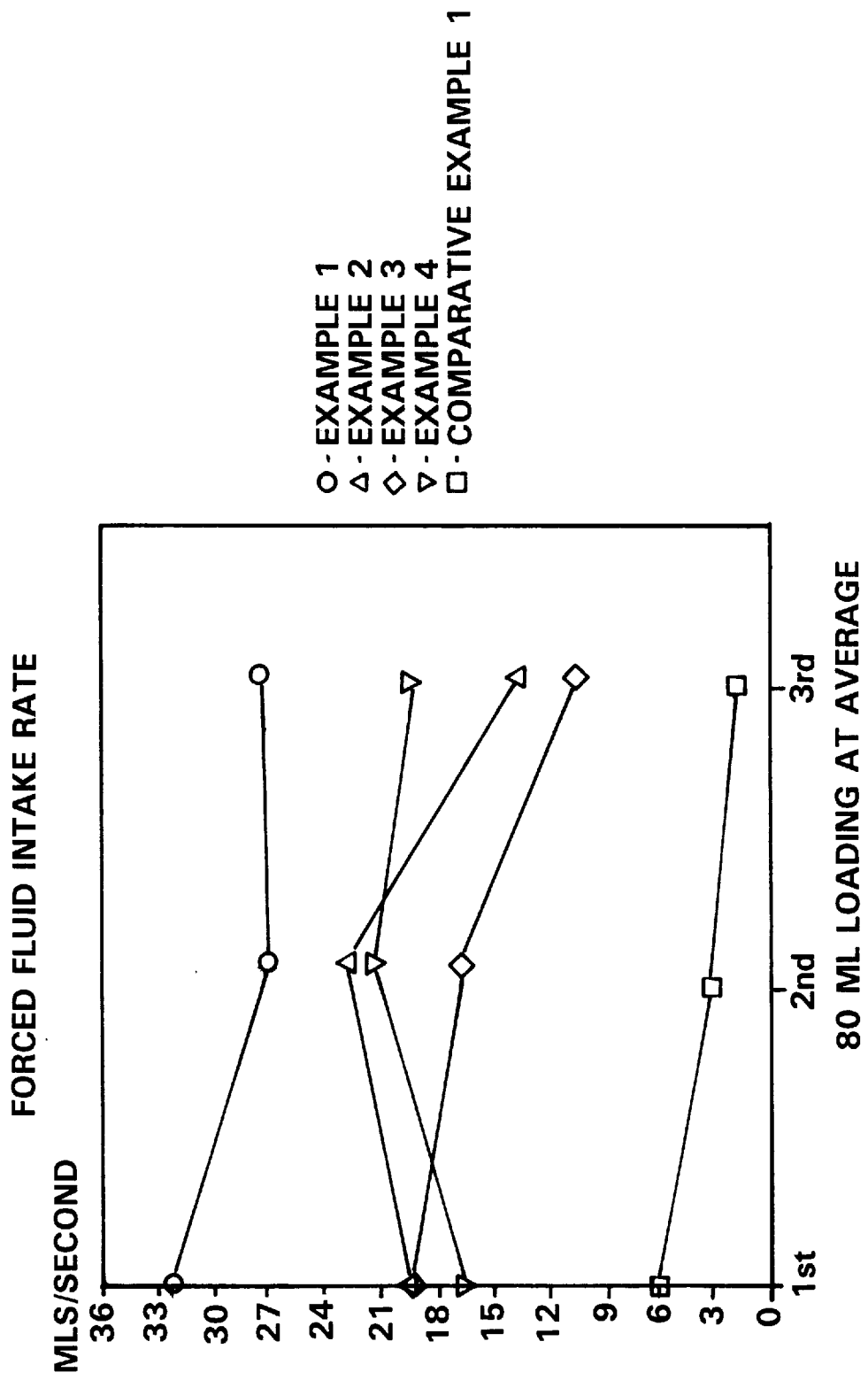
FIG. 10 representatively shows a graph of the data obtained in the Examples demonstrating the fluid intake rate for three loadings.

The diaper was then subjected to the Forced Fluid Intake Test as described above. The diaper had a fluid intake rate of about 32 milliliters per second for the first insult (80 ml), about 27 milliliters per second for the second insult (80 ml) and about 27 milliliters per second for the third insult (80 ml). The results are shown in the graph of FIG. 10.

Twenty samples of the same diaper were then tested on twenty different infants to measure the ability of the diaper to contain fluids prior to leaking or overflowing onto the outer clothing of the wearer. The diapers were placed on the infants. At five minute intervals, 30 milliliters of saline (0.9 weight percent solution of sodium chloride in distilled water) was injected into the diaper until the diaper leaked. The net fluid weight injected into the diaper (load-at-leak) was then recorded. The leakage data is representatively illustrated in FIG. 11.

EXAMPLE 2

A medium size diaper suitable for an infant weighing about 13–23 lbs. comprised a 1 mil thick outer cover composed of polyethylene film, a composite absorbent core of the present invention, and a bodyside liner composed of a spunbonded material. The bodyside liner was a nonwoven, spunbond, polypropylene fabric composed of about 2.8–3.2 denier fibers formed into a web having a basis weight of about 22 grams per square meter and a density of about 0.06 grams per cubic centimeter. The bodyside liner was surface treated with about 0.28 weight percent of a surfactant commercially available from Rohm and Haas Co. under the trade designation Triton X-102.

The composite absorbent core was arranged according to the configuration representatively illustrated in FIGS. 2 and 3 and sandwiched between the outer cover and bodyside liner. The absorbent portion 60 included about 10.9 grams of wood pulp fluff and 10.9 grams of a high-absorbency material. The absorbent portion had a basis weight of 530 grams per square meter and covered an area of 162.6 square centimeters (64.0 square inches). The high-absorbency material was IM5000 which was commercially available from Hoechst-Celanese.

The porous resilient portion 62 was the polyurethane foam material described in Example 1 as Material A. The porous resilient portion had a basis weight of 160 grams per square meter and a density of 0.027 grams per cubic centimeter. The porous resilient portion had a length dimension of 20.3 centimeters (8.0 inches) and a width dimension of 8.9 centimeters (3.5 inches). The porous resilient portion was substantially centered about the longitudinal centerline 56 and transverse centerline 58 of the composite absorbent core. The composite absorbent core had a narrow crotch width dimension of 3.18 centimeters (1.25 inches).

The diaper was then subjected to the Forced Fluid Intake Test as described above. The diaper had a fluid intake rate of about 20 milliliters per second for the first insult (80 ml), about 23 milliliters per second for the second insult (80 ml) and 13 milliliters per second for the third insult (80 ml). The results are shown in the graph of FIG. 10.

EXAMPLE 3

A medium size diaper suitable for an infant weighing about 13–23 lbs. comprised a 1 mil thick outer cover composed of polyethylene film, a composite absorbent core of the present invention, and a bodyside liner composed of a spunbonded material. The bodyside liner was a nonwoven, spunbond, polypropylene fabric composed of about 2.8–3.2 denier fibers formed into a web having a basis weight of about 22 grams per square meter and a density of about 0.06 grams per cubic centimeter. The bodyside liner was surface treated with about 0.28 weight percent of a surfactant commercially available from Rohm and Haas Co. under the trade designation Triton X-102.

The composite absorbent core was arranged according to the configuration representatively illustrated in FIGS. 4 and 5 and sandwiched between the outer cover and bodyside liner. The absorbent portion 60 included about 10.9 grams of wood pulp fluff and 10.9 grams of a high-absorbency material. The absorbent portion had a basis weight of 530 grams per square meter and covered an area of 162.6 square centimeters (64.0 square inches). The high-absorbency material was IM5000 which was commercially available from Hoechst-Celanese.

The porous resilient portion 62 was the polyurethane foam material described in Example 1 as Material A. The porous resilient portion had a basis weight of 160 grams per square meter and a density of 0.027 grams per cubic centimeter. The porous resilient portion had a length dimension of 20.3 centimeters (8.0 inches) and a width dimension of 8.9 centimeters (3.5 inches).

The surge portion 70 was composed of a through-air bonded carded web material which was the same as that described in Example 1 as Comparative Material A except that it had a basis weight of 150 grams per square meter and a density of 0.056 grams per cubic centimeter. The surge portion also had a length dimension of 10.2 centimeters (4.0 inches) and a width dimension of 7.6 centimeters (3.0 inches).

The porous resilient portion and surge portion were substantially centered about the longitudinal centerline 56 and transverse centerline 58 of the composite absorbent core. The composite absorbent core had a narrow crotch width dimension of 3.18 centimeters (1.25 inches).

The diaper was then subjected to the Forced Fluid Intake Test as described above. The diaper had a fluid intake rate of about 20 milliliters per second for the first insult (80 ml), about 17 milliliters per second for the second insult (80 ml) and about 11 milliliters per second for the third insult (80 ml). The results are shown in the graph of FIG. 10.

EXAMPLE 4

A medium size diaper suitable for an infant weighing about 13–23 lbs. comprised a 1 mil thick outer cover composed of polyethylene film, a composite absorbent core of the present invention, and a bodyside liner composed of a spunbonded material. The bodyside liner was a nonwoven, spunbond, polypropylene fabric composed of about 2.8–3.2 denier fibers formed into a web having a basis weight of about 22 grams per square meter and a density of about 0.06 grams per cubic centimeter. The bodyside liner was surface treated with about 0.28 weight percent of a surfactant commercially available from Rohm and Haas Co. under the trade designation Triton X-102.

The composite absorbent core was arranged according to the configuration representatively illustrated in FIG. 6 and sandwiched between the outer cover and bodyside liner. The first absorbent portion 102 included about 3.65 grams of wood pulp fluff and 3.65 grams of a high-absorbency material. The first absorbent portion had a basis weight of 530 grams per square meter and covered an area of 54.0 square centimeters (21.25 square inches). The second absorbent portion 104 included about 7.3 grams of wood pulp fluff and 7.3 grams of a high-absorbency material. The second absorbent portion had a basis weight of 530 grams per square meter and covered an area of 108.6 square centimeters (42.75 square inches). The high-absorbency material was IM5000 which was commercially available from Hoechst-Celanese.

The porous resilient portion 108 was composed of the polyurethane foam material described in Example 1 as Material A. The porous resilient portion had a basis weight of 160 grams per square meter and a density of 0.027 grams per cubic centimeter. The porous resilient portion had a length dimension of 20.3 centimeters (8.0 inches) and a width dimension of 8.9 centimeters (3.5 inches).

The first surge portion 112 and second surge portion 114 were similar to the through-air bonded carded web material described in Example 1 as Comparative Material A except that they had a basis weight of 150 grams per square meter and a density of 0.056 grams per cubic centimeter. The first and second surge portions also had a length dimension of 20.3 centimeters (8.0 inches) and a width dimension of 8.9 centimeters (3.5 inches).

The porous resilient portion and surge portions were substantially centered about the longitudinal centerline 56 and transverse centerline 58 of the composite absorbent core. The composite absorbent core had a narrow crotch width dimension of 3.18 centimeters (1.25 inches).

The diaper was then subjected to the Forced Fluid Intake Test as described above. The diaper had a fluid intake rate of about 17 milliliters per second for the first insult (80 ml), about 22 milliliters per second for the second insult (80 ml) and about 20 milliliters per second for the third insult (80 ml). The results are shown in the graph of FIG. 10.

Comparative Example 1

A medium size diaper suitable for an infant weighing about 13–23 lbs. comprised a 1 mil thick outer cover composed of polyethylene film, an absorbent structure, and a bodyside liner composed of a spunbonded material. The bodyside liner was a nonwoven, spunbond, polypropylene fabric composed of about 2.8–3.2 denier fibers formed into a web having a basis weight of about 22 grams per square meter and a density of about 0.06 grams per cubic centimeter. The bodyside liner was surface treated with about 0.28 weight percent of a surfactant commercially available from Rohm and Haas Co. under the trade designation Triton X-102.

The absorbent structure included about 12.0 grams of wood pulp fluff and 12.0 grams of a high-absorbency material. The absorbent structure had a basis weight of 830 grams per square meter and a density of 0.15 grams per cubic centimeter. The high-absorbency material was IM5000 superabsorbent material available from Hoechst- Celanese. The absorbent structure was sandwiched between the outer cover and bodyside liner. The absorbent structure had a narrow crotch width dimension of 3.18 centimeters (1.25 inches).

A surge management layer was placed between the bodyside liner and the absorbent structure. The surge management layer was composed of a through-air bonded carded web material similar to the material described in Example 1 as Comparative Material A except that it had a basis weight of 150 grams per square meter and a density of 0.056 grams per cubic centimeter. The surge layer had a length dimension of 374 centimeters (14.75 inches) and a width dimension of 10.2 centimeters (4.0 inches).

The diaper was then subjected to the Forced Fluid Intake Test as described above. The diaper had a fluid intake rate of 6 milliliters per second for the first insult (80 ml), 3 milliliters per second for the second insult (80 ml) and 2 milliliters per second for the third insult (80 ml). The results are shown in the graph of FIG. 10.

Twenty samples of the same diaper were then tested on twenty different infants to measure the ability of the diaper to contain fluids prior to leaking or overflowing onto the outer clothing of the wearer. The diapers were placed on the infants. At five minute intervals, 30 milliliters of saline (0.9 weight percent solution of sodium chloride in distilled water) was injected into the diaper until the diaper leaked. The net fluid weight injected into the diaper (load-at-leak) was then recorded. The leakage data is representatively illustrated in FIG. 11.

As is shown in FIG. 10, the composite absorbent core and absorbent article of the different aspects of the present invention has an improved fluid intake rate when compared to typical absorbent articles using conventional absorbent structures having similar narrow crotch widths. Further, as is illustrated in FIG. 11, the composite absorbent core and absorbent article of the present invention are better able to absorb and contain urine upon multiple insults. The in-use tests showed significantly improved leakage reduction in diapers using composite absorbent cores which include at least one porous resilient portion as described above. This data clearly demonstrates the desirability of employing porous resilient portions in diapers having very narrow crotch widths.

Thus, the composite absorbent core of the present invention advantageously provides a resilient composite absorbent structure which has a relatively narrow crotch width and is capable of efficiently receiving and distributing fluids to more effectively utilize the absorbent capacity of the absorbent article. The narrow crotch width of the absorbent core provides an absorbent article having a conforming, comfortable fit about the wearer which is also aesthetically pleasing.

While the invention has been described in detail with respect to specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

What is claimed is:

1. A composite absorbent core suitable for use in an absorbent article, said absorbent core having a front section, a back section and a crotch section which extends between and connects said front section to said back section, said absorbent core comprising:

a) at least one absorbent portion; and
b) at least one porous resilient portion which has a void volume of at least about 3 cubic centimeters when under no load and is located adjacent said at least one absorbent portion wherein said at least one porous resilient portion comprises an open-celled foam material which has a wet compression recovery of at least about 85 percent as determined according to a Wet Compression Recovery Test as described herein.

2. The absorbent core according to claim 1 wherein said at least one absorbent portion includes at least about 25 weight percent of a high-absorbency material based on a total weight of said at least one absorbent portion.

3. The absorbent core according to claim 1 wherein said wet compression recovery of said at least one porous resilient portion is from about 90 to about 100 percent.

4. The absorbent core according to claim 1 wherein said at least one porous resilient portion has a basis weight of from about 100 to about 200 grams per square meter and a density which is no more than about 0.050 grams per cubic centimeter.

5. The absorbent core according to claim 1 wherein said void volume of said at least one porous resilient portion is from about 5 to about 9 cubic centimeters when under no load.

6. The absorbent core according to claim 1 wherein said at least one porous resilient portion has a void volume of at least about 20 cubic centimeters per gram when under no load.

7. The absorbent core according to claim 1 wherein said foam material is a semi-rigid, polyurethane open-celled foam material wherein at least 80 percent of the cells present in said foam material are open cells.

8. The absorbent core according to claim 1 wherein said at least one porous resilient portion is substantially hydrophobic.

9. The absorbent core according to claim 1 wherein said at least one porous resilient portion has a mean pore size of at least about 1.50 millimeters as determined according to a Pore Size Test as described herein.

10. The absorbent core according to claim 1 wherein said at least one porous resilient portion is capable of maintaining at least about 25 percent of said void volume when under a load of 0.673 Newtons per square centimeter (0.975 pounds per square inch).

11. The absorbent core according to claim 1 wherein said absorbent core has a fluid intake rate of at least about 10 milliliters per second as determined according to a Forced Fluid Intake Test as described herein.

12. The absorbent core according to claim 1 wherein said absorbent core has a crotch width dimension which is no more than about 6.35 centimeters (2.50 inches).

13. The absorbent core according to claim 1 and further comprising at least one surge portion which is located adjacent said at least one porous resilient portion and has a basis weight of from about 30 to about 240 grams per square meter and a density which is not more than about 0.10 grams per cubic centimeter.

14. The absorbent core according to claim 13 wherein said at least one surge portion comprises a layer of through-air bonded carded web material which has a mean pore size of from about 0.20 to about 1.00 millimeters as determined according to a Pore Size Test as described herein.

15. A composite absorbent core suitable for use in an absorbent article, said absorbent core having a front section, a back section and a crotch section which extends between and connects said front section to said back section, said absorbent core comprising:

a) a first absorbent portion which is located in said back section and said crotch section of said absorbent core;

b) a second absorbent portion which is located in said front section of said absorbent core and not in said back section of said absorbent core; and c) a first porous resilient portion which has a void volume and is located between said first and said second absorbent portions wherein said first porous resilient portion has a wet compression recovery of at least about 85 percent as determined according to a Wet Compression Recovery Test as described herein.

16. The absorbent core according to claim 15 wherein said first and said second absorbent portion include at least about 25 weight percent of a high-absorbency material based on a total weight of said first and said second absorbent portion.

17. The absorbent core according to claim 15 wherein said wet compression recovery of said first porous resilient portion is from about 90 to about 100 percent.

18. The absorbent core according to claim 15 wherein said first porous resilient portion is capable of maintaining at least about 25 percent of said void volume when under a load of 0.673 Newtons per square centimeter (0.975 pounds per square inch).

19. The absorbent core according to claim 15 wherein said first porous resilient portion has a void volume of at least about 20 cubic centimeters per gram when under no load.

20. The absorbent core according to claim 15 wherein said first porous resilient portion has a basis weight of from about 100 to about 200 grams per square meter and a density of not more than about 0.050 grams per cubic centimeter.

21. The absorbent core according to claim 15 wherein said first porous resilient portion has a mean pore size of at least about 1.50 millimeters as determined according to a Pore Size Test as described herein.

22. The absorbent core according to claim 15 wherein said absorbent core has a fluid intake rate of at least about 10 milliliters per second as determined according to a Forced Fluid Intake Test as described herein.

23. The absorbent core according to claim 15 wherein said absorbent core has a crotch width dimension which is no more than 6.35 centimeters (2.50 inches).

24. The absorbent core according to claim 15 and further comprising at least one surge portion which is located adjacent said first absorbent portion and has a basis weight of from about 30 to about 240 grams per square meter and a density of not more than about 0.10 grams per cubic centimeter.

25. The absorbent core according to claim 24 wherein said at least one surge portion comprises a layer of through-air bonded carded web material which has a mean pore size of from about 0.20 to about 1.00 millimeters as determined according to a Pore Size Test as described herein.

26. The absorbent core according to claim 15 and further comprising:

a) a third absorbent portion which is located underneath said first and said second absorbent portions and extends substantially along an entire length of said absorbent core; and b) a second porous resilient portion which is located between said second absorbent portion and said third absorbent portion wherein said second porous resilient portion has a wet compression recovery of at least about 85 percent as determined according to a Wet Compression Recovery Test as described herein.

27. An absorbent article having a front portion, a rear portion and a crotch portion which extends between and connects said front portion to said rear portion, said absorbent article comprising:

a) an outer cover;

b) a bodyside liner which is superposed on said outer cover; and c) a composite absorbent core which is located between said outer cover and said bodyside liner wherein said absorbent core comprises:

1) at least one absorbent portion; and 2) at least one porous resilient portion which has a void volume and is located adjacent said at least one absorbent portion wherein said at least one porous resilient portion has a mean pore size of at least about 1.50 millimeters as determined according to a Pore Size Test as described herein and a wet compression recovery of at least about 85 percent as determined according to a Wet Compression Recovery Test as described herein.

28. The absorbent article according to claim 27 wherein said at least one absorbent portion includes at least about 25 weight percent of a high-absorbency material based on a total weight of said at least one absorbent portion.

29. The absorbent article according to claim 27 wherein said wet compression recovery of said at least one porous resilient portion is from about 90 to about 100 percent.

30. The absorbent article according to claim 27 wherein said at least one porous resilient portion has a mean pore size of from about 2.0 to about 4.0 millimeters as determined according to the Pore Size Test.

31. The absorbent article according to claim 27 wherein said absorbent article has a fluid intake rate of at least about 10 milliliters per second as determined according to a Forced Fluid Intake Test as described herein.

32. The absorbent article according to claim 27 wherein said absorbent article has an article crotch width dimension which is no more than 12.7 centimeters (5.0 inches).

33. The absorbent article according to claim 27 and further comprising at least one surge portion which is located adjacent said at least one porous resilient portion and has a basis weight of from about 30 to about 240 grams per square meter and a density of no more than about 0.10 grams per cubic centimeter.

34. An absorbent article having a front portion, a rear portion and a crotch portion which extends between and connects said front portion to said rear portion, said absorbent article comprising:

a) an outer cover;

b) a bodyside liner which is superposed on said outer cover; and c) a composite absorbent core which is located between said outer cover and said bodyside liner and which has a front section, a back section and a crotch section which extends between and connects said front section to said back section, wherein said absorbent core comprises:

1) a first absorbent portion which is located in said back section and said crotch section of said absorbent core;

2) a second absorbent portion which is located in said front section of said absorbent core; and 3) a first porous resilient portion which has a void volume and is located between said first and said second absorbent portions wherein said first porous resilient portion comprises an open-celled foam material which has a wet compression recovery of at least about 85 percent as determined according to a Wet Compression Recovery Test as described herein.

35. The absorbent article according to claim 34 wherein said first porous resilient portion has a wet compression recovery of from about 90 to about 100 percent as determined according to the Wet Compression Recovery Test.

36. The absorbent article according to claim 34 wherein said first porous resilient portion has a basis weight of from about 100 to about 200 grams per square meter and a density of not more than about 0.050 grams per cubic centimeter.

37. The absorbent article according to claim 34 wherein said first porous resilient portion has a void volume of at least about 20 cubic centimeters per gram when under no load.

38. The absorbent article according to claim 34 wherein said absorbent article has a fluid intake rate of at least about 10 milliliters per second as determined according to a Forced Fluid Intake Test as described herein.

39. The absorbent article according to claim 34 wherein said absorbent article has an article crotch width dimension which is no more than 12.7 centimeters (5.00 inches).

40. The absorbent article according to claim 34 wherein said absorbent core further comprises:
   a) a third absorbent portion which is located underneath said first and said second absorbent portions and extends substantially along an entire length of said absorbent core; and
   b) a second porous resilient portion which is located between said second absorbent portion and said third absorbent portion wherein said second porous resilient portion has a wet compression recovery of at least about 85 percent as determined according to the Wet Compression Recovery Test.

41. The absorbent article according to claim 40 and further comprising at least one surge portion which is located adjacent said first absorbent portion and has a basis weight of from about 30 to about 240 grams per square meter and a density of no more than about 0.10 grams per cubic centimeter.

42. A composite absorbent core suitable for use in an absorbent article, said absorbent core having a front section, a back section and a crotch section which extends between and connects said front section to said back section, said absorbent core comprising:
   a) a first absorbent portion which is located in said back section and said crotch section of said absorbent core;
   b) a second absorbent portion which is located in said front section of said absorbent core;
   c) a first porous resilient portion which has a void volume and is located between said first and said second absorbent portions wherein said first porous resilient portion has a wet compression recovery of at least about 85 percent as determined according to a Wet Compression Recovery Test as described herein, and
   d) at least one surge portion which is located adjacent said first absorbent portion and has a basis weight of from about 30 to about 240 grams per square meter and a density of not more than about 0.10 grams per cubic centimeter.

43. The absorbent core according to claim 42 wherein said wet compression recovery of said first porous resilient portion is from about 90 to about 100 percent.

44. The absorbent core according to claim 42 wherein said first porous resilient portion is capable of maintaining at least about 25 percent of said void volume when under a load of 0.673 Newtons per square centimeter (0.975 pounds per square inch).

45. The absorbent core according to claim 42 wherein said first porous resilient portion has a void volume of at least about 20 cubic centimeters per gram when under no load.

46. The absorbent core according to claim 42 wherein said first porous resilient portion has a basis weight of from about 100 to about 200 grams per square meter and a density of not more than about 0.050 grams per cubic centimeter.

47. The absorbent core according to claim 42 wherein said first porous resilient portion has a mean pore size of at least about 1.50 millimeters as determined according to a Pore Size Test as described herein.

48. The absorbent core according to claim 42 wherein said absorbent core has a fluid intake rate of at least about 10 milliliters per second as determined according to a Forced Fluid Intake Test as described herein.

49. The absorbent core according to claim 42 wherein said absorbent core has a crotch width dimension which is no more than 6.35 centimeters (2.50 inches).

50. The absorbent core according to claim 42 wherein said at least one surge portion comprises a layer of through-air bonded carded web material which has a mean pore size of from about 0.20 to about 1.00 millimeters as determined according to a Pore Size Test as described herein.

51. The absorbent core according to claim 42 and further comprising:
   a) a third absorbent portion which is located underneath said first and said second absorbent portions and extends substantially along an entire length of said absorbent core; and
   b) a second porous resilient portion which is located between said second absorbent portion and said third absorbent portion wherein said second porous resilient portion has a wet compression recovery of at least about 85 percent as determined according to the Wet Compression Recovery Test.

* * * * *